United States Patent [19]

Rao et al.

[11] Patent Number: 4,921,801
[45] Date of Patent: May 1, 1990

[54] NOVEL RECOMBINANT DNA COSMID SHUTTLE VECTORS

[75] Inventors: R. Nagaraja Rao, Indianapolis; Richard K. Stanzak, Poland, both of Ind.

[73] Assignee: Eli Lilly and Company, Indianapolis, Ind.

[21] Appl. No.: 842,102

[22] Filed: Mar. 20, 1986

Related U.S. Application Data

[63] Continuation-in-part of Ser. No. 742,172, Jun. 7, 1985, abandoned, which is a continuation-in-part of Ser. No. 655,178, Sep. 27, 1984, abandoned.

[51] Int. Cl.$^5$ .................... C12N 15/00; C12N 1/20; C12N 7/00
[52] U.S. Cl. ........................ 435/172.3; 435/252.33; 435/252.35; 435/320; 435/849; 435/889; 935/26; 935/73; 935/75; 935/80
[58] Field of Search ............ 435/172.3, 253, 320, 435/849, 886, 889; 935/26, 73, 75

[56] References Cited

U.S. PATENT DOCUMENTS 4,304,863 12/1981 Collins et al. .................. 435/172
4,460,689 7/1984 Foor et al. .................... 435/172

FOREIGN PATENT DOCUMENTS 146368 6/1985 European Pat. Off. .

OTHER PUBLICATIONS

Collins, J. et al., 1978, Proc. Natl. Acad. Sci. 75:4242.
Bates, P. et al., 1983, Gene 26:137.
Frey, J. et al., 1983, Gene 24:299.
Tandeau de Marsac, N., 1982, Gene 20:111.
Manis, J. et al., Abstracts of the Annual Meeting of American Society for Microbiology 1984, 84th Annual Meeting, St. Louis, Missouri, p. 119.
Bibb et al. in *Experimental Manipulation of Gene Expression*, M. Inouye ed., (Academic Press, N.Y.) 1983, pp. 53–67 and 79–82.
Kolter et al. *Ann Rev. Genet.* 13:355–62, 67, 68 and 382–391, 1979.
Chambers A. et al., Construction and Use of a Bifunctional Streptomycete Cosmid, 1984, Biochemical Society Transactions, 607th Meeting, London, vol. 12, pp. 644–645.
Collins J. et al., 1978, Gene 4:85–107.
Poustka et al., 1984, *Proc. Natl. Acad. Sci. U.S.A.* 81:4129–4133.
Lydiate et al., 1985, Gene 35:223–235.

Primary Examiner—Thomas D. Mays
Attorney, Agent, or Firm—Joseph A. Jones; Ron K. Levy; Leroy Whitaker

[57] ABSTRACT

Novel recombinant DNA cosmid shuttle vectors and a method of using them in the construction of genomic DNA libraries are described. The vectors demonstrate the incorporation of both the size selection and in vitro packaging mechanisms of lambda into a Streptomyces-*E. coli* shuttle vector by the incorporation of two or more COS sequences of bacteriophage lambda.

58 Claims, 14 Drawing Sheets

Restriction Site and
Function Map of Cosmid
pKC420 (10657 bp)

Restriction Site and Function Map of Cosmid pKC420 (10657 bp)

Construction of a Genomic DNA Library**

Restriction Site and Function Map of Cosmid pKC427 (11654 bp)

Restriction Site and Function Map of Cosmid pKC428 (13154 bp)

Restriction Site and
Function Map of Cosmid
pKC448 (11654 bp)

Restriction Site and Function Map of Cosmid pKC462 (11487 bp)

Restriction Site and
Function Map of Cosmid
pKC467 (11027 bp)

Restriction Site and Function Map of Plamid pKC462A (12.4 Kb)

Restriction Site and
Function Map of Plasmid
pOJ108    (12.7 Kb)

Restriction Site and Function Map of Plasmid pOJ111 (11.7 Kb)

Restriction Site and
Function Map of Cosmid
cos111 (14.3 Kb)

Restriction Site and Function Map of Plasmid pKC513 (11.5 Kb)

Restriction Site and
Function Map of Plasmid
pKC578 (10.3 Kb)

NOVEL RECOMBINANT DNA COSMID SHUTTLE VECTORS

CROSS REFERENCE

This application is a continuation-in-part of our co-pending U.S. application Ser. No. 742,172, filed June 7, 1985, abandoned, which is a continuation-in-part of U.S. application Ser. No. 655,178, filed Sept. 27, 1984, abandoned.

SUMMARY OF THE INVENTION

The present invention comprises novel recombinant DNA cosmid shuttle vectors comprising replicons that are functional in *Escherichia coli* and Streptomyces, a DNA segment that contains two or more cos elements of bacteriophage lambda and one or more DNA segments that convey resistance to antibiotics. The invention further comprises transformants of the aforementioned vectors. A method of using the cosmid shuttle vectors to construct genomic DNA libraries is also disclosed.

Cosmids are vectors specifically designed for cloning large fragments of DNA. These vectors are modified plasmids which contain a plasmid replicon, a selectable drug resistance marker and the lambda cos site. Due to their relatively small size and the presence of the lambda cos element, cosmids can accept inserts of up to 30–45 kilobases (kb) and utilize the lambda in vitro packaging system to positively select for large size inserts. Thus, these vectors provide an efficient mechanism to introduce foreign DNA into bacterial cells.

The present invention provides antibiotic resistance conferring cosmid vectors that contain bifunctional replicons for use in *E. coli* and Streptomyces host cells. Bifunctional constructions are particularly advantageous because amplification and manipulation of vectors can be done faster and more conveniently in *E. coli* than in Streptomyces. Thus, after desired recombinant DNA procedures are accomplished within the *E. coli* host system, the particular plasmid DNA can be removed and then transformed into a Streptomyces host cell. It may also be possible to directly transfer the plasmid DNA to a Streptomyces host cell by means of a cell-to-cell fusion or phage particle-to-cell fusion. Gene cloning and expression of products in Streptomyces are highly advantageous since the organism is substantially non-pathogenic and ordinarily does not produce endotoxins. Heretofore, the development and exploitation of recombinant DNA technology in the above organisms has been retarded and time-consuming because of the general lack of efficient cloning systems available to accommodate large segments of DNA. The vectors of the present invention can accommodate large inserts of DNA, are functional as well as selectable in both Streptomyces and *E. coli* host strains and therefore represent a significant advance in the technical art.

The present invention further provides cosmid cloning vectors which contain multiple lambda cos sites. The presence of multiple cos sites on a single vector eliminates the need to prepare separate cosmid arms. The construction of genomic libraries is thereby facilitated by the structural composition of the present vectors. The present invention also provides a convenient method to construct genomic DNA libraries using the cosmid shuttle vectors of the present invention. Presently, there are three systems available for use in genomic DNA library construction: transformation of a bacterial cell by plasmid DNA (L. Clark and J. Carbon, 1976, *Cell* 9:91); transduction of a bacterial cell by lambda bacteriophage vectors (Lawn et al., 1978, *Cell* 15:1157); and transduction of a bacterial cell by cosmid vectors (Collins et al., 1978, *Proc. Natl. Acad. Sci.*, 75:4242). However, λ vectors are limited in their ability to accommodate DNA inserts of up to 20 kb and large plasmids have low transformation efficiencies. Thus, the use of cosmid vectors to clone large DNA fragments is preferred over both plasmid and λ bacteriophage vectors. There is a twofold advantage of using cosmid vectors to construct genomic libraries over plasmid or lambda bacteriophage vectors. First, the ability of a cosmid vector to accommodate large DNA inserts preserves the original linkage relationships of the inserted genome. This preservation is, however, dependent on the details of the cloning procedure and is independent on the cloning system. Since larger inserts cover the entire genome, statistically, in a limited number of colonies, the screening process is thereby reduced. Secondly, the relative ease of preparation of DNA confers a beneficial advantage to the present cosmid vectors.

The specific advantage of the method according to the invention over known cosmid vectors is the ability of the present vectors to be grown and amplified in *E. coli* and then shuttled into Streptomyces host cells for subsequent functional analysis of the cloned DNA. The vectors are relatively small, versatile and can transform and be selected in any Streptomyces cell that is sensitive to an antibiotic for which resistance is conveyed and wherein the Streptomyces plasmid origin of replication is functional. Since more than seventy percent of naturally occurring antibiotics are produced by Streptomyces strains, it is desirable to develop cloning systems and vectors that are applicable to that industrially important group. The present invention provides such vectors and thus allows for the shuttling and cloning of genes into Streptomyces both for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among millions of cells, has acquired the plasmid DNA. This is important because the foreign DNA sequences that are themselves non-selectable can be inserted into the vectors and, upon transformation, cells containing the vector and the particular DNA sequence of interest can be isolated by appropriate phenotypic selection.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Cosmid—a plasmid carrying the ligated cohesive ends (cos) of bacteriophage; as a result, the plasmid DNA can be packaged either in vitro in the phage coat or in vivo using suitable *E. coli* strains.

cos sequence—a cohesive end site comprising a 12 bp sequence from bacteriophage lambda that is recognized by the lambda-specific packaging proteins.

Library—a collection of cloned fragments of DNA, which together represent an entire genome.

Restriction Fragment—any linear DNA generated by the action of one or more restriction enzymes.

Sensitive Host Cell—a host cell that cannot grow in the presence of a given antibiotic without a DNA segment that confers resistance thereto.

Transformation—the introduction of DNA into a recipient host cell that changes the genotype and consequently results in a change in the recipient cell.

Transformant—a recipient host cell that has undergone transformation.

E. coli Replicon—a DNA sequence that controls and allows for replication of a plasmid or other vector in E. coli.

Streptomyces Replicon—a DNA sequence that controls and allows for replication of a plasmid or other vector in Streptomyces.

$Ap^R$—the ampicillin resistant phenotype.
$Am^R$—the apramycin resistant phenotype.
$Tsr^R$—the thiostrepton resistant phenotype.
$Nm^R$—the neomycin resistant phenotype.
Ori—a plasmid origin of replication.

DETAILED DESCRIPTION OF THE INVENTION

The present invention comprises recombinant DNA cosmid shuttle vectors comprising:
(a) a replicon that is functional in E. coli,
(b) a replicon that is functional in Streptomyces,
(c) a DNA segment that contains two or more cos sequences of bacteriophage lambda, and
(d) one or more DNA segments that convey resistance to at least one antibiotic when transformed into a sensitive restrictionless host cell.

The invention further comprises transformants of the aforementioned vectors.

Vectors of the present invention represent novel hybrids between a Streptomyces vector and a cosmid. For example, cosmid vector pKC420 can replicate autonomously in Streptomyces and in E. coli since it contains replicons from both organisms. In addition, selectable markers are present for both organisms ($Ap^R$ in E. coli and $Am^R$ in both E. coli and Streptomyces) providing a convenient means to select for transformants. Furthermore, the bacteriophage lambda cos sequences allow the vector to be packaged in vitro and transformed into E. coli. The recombinant plasmids can then be used to transform Streptomyces host cells. Thus, given the presence of λ cos sequences in the present shuttle vectors, the cloning advantages inherent to cosmid vectors are now applicable to Streptomyces.

Figure 1:
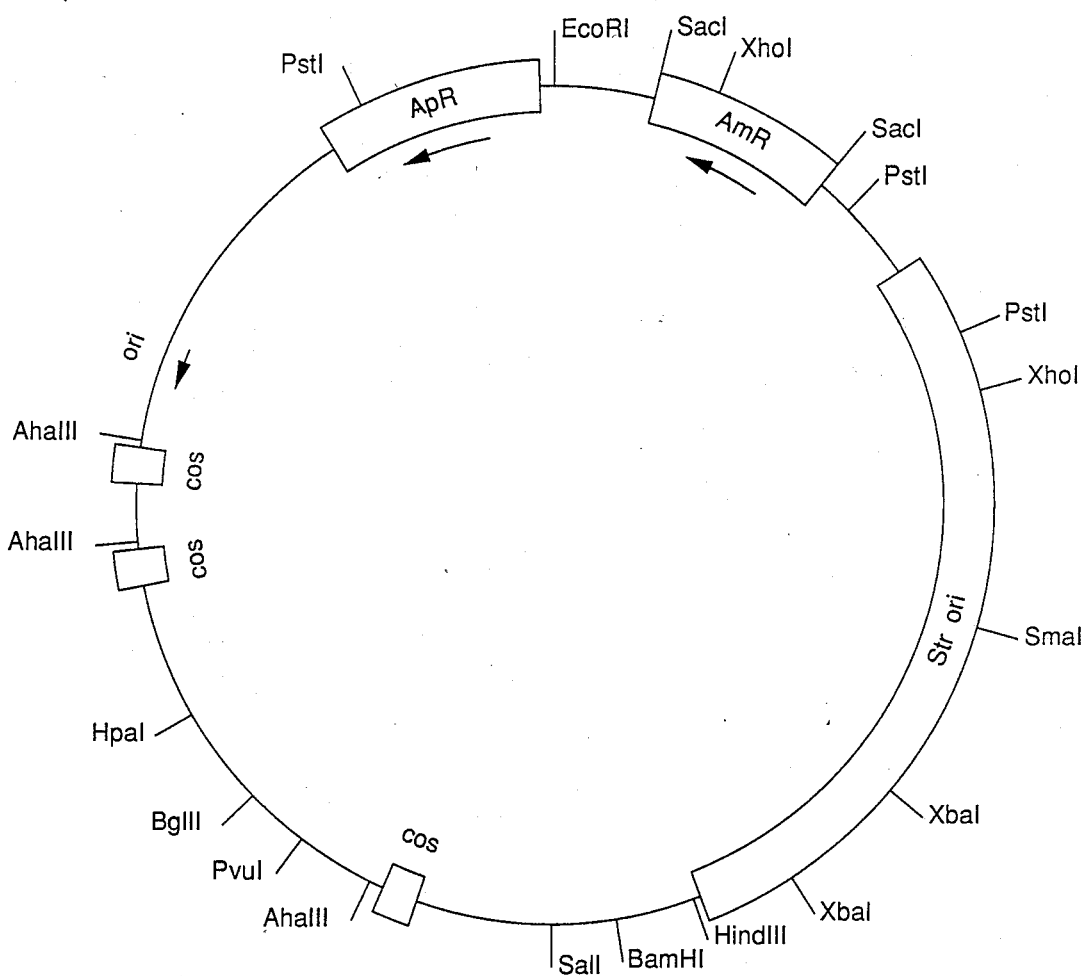
FIG. 1 shows the restriction site and function map of cosmid pKC420.

Cosmid shuttle vector pKC420 is approximately 10.6 kb and contains several restriction sites which are particularly advantageous for molecular cloning. Cosmid pKC420 can be conventionally isolated from E. coli K12 DH1/pKC420, a constructed strain deposited and made part of the stock culture collection of the Northern Regional Research Laboratory, Peoria, Ill. 61604. It is available to the public as a source and stock reservoir of the cosmid under the accession number NRRL B-15837. A detailed restriction site and functional map of cosmid pKC420 is presented in FIG. 1 of the accompanying drawings. For purposes of the present application, FIG. 1 and all subsequent figures are not drawn to scale.

Cosmid pKC420, useful directly as a cloning vector, can also be used to construct derivative vectors within the scope of the present invention. Cosmid pKC420 can be restricted and ligated to one or more antibiotic resistance conferring DNA fragments, exemplified herein for illustrative purposes by the thiostrepton resistance conferring ~1 kb BclI restriction fragment of plasmid pIJ702 (ATCC 39155), the Tn903 neomycin resistance conferring ~1.5 kb EcoRI restriction fragment of plasmid pUC4K (NRRL B-15836), and the Tn5 neomycin resistance conferring ~1.5 kb HindIII-SalI restriction fragment of plasmid pKC7 (ATCC 37084), to form vectors illustrative of the present invention. Plasmids pIJ702 and pKC7 can be isolated from strains deposited and made part of the stock culture collection of the American Type Culture Collection, Rockville, Md. 20852, and are available to the public as a source and stock reservoir of their plasmids under the accession numbers ATCC 39155 and 37084, respectively. Plasmid pUC4K, the source of the neomycin resistance conferring fragment, is a strain deposited and made part of the stock culture collection of the Northern Regional Research Laboratory, Peoria, Ill. 61604 and is available to the public as a source and stock reservoir of the plasmid under the accession number NRRL B-15836.

For convenience and ease of construction, the thiostrepton resistance conferring ~1 kb BclI fragment is inserted into cosmid pKC420 at the unique BamHI restriction site. The resulting recombinant DNA is then ligated to produce cosmids illustrative of the present invention. Phenotypically desired recombinant plasmids of two orientations result depending upon the orientation of the inserted DNA fragment. Thus, the insertion of the ~1 kb BclI restriction fragment into cosmid pKC420 results in illustrative cosmids pKC427 and pKC427A.

Various cosmid pKC420 restriction sites can be used for the insertion of DNA segments provided that the replicons, selectable markers and other necessary plasmid functions are not disrupted. Those skilled in the art understand or can readily determine which sites are advantageous for the ligation or insertion of a particular DNA segment.

Although the thiostrepton and neomycin antibiotic resistance conferring DNA segments are, for illustrative purposes, respectfully exemplified by the ~1 kb BclI restriction fragment of pIJ702, the ~1.5 kb EcoRI restriction fragment of plasmid pUC4K, and the ~1.5 kb HindIII-SalI restriction fragment of plasmid pKC7, those skilled in the art can construct and substitute either individually or in combination, other DNA segments that also confer resistance to the aforementioned antibiotics. Other thiostrepton resistance conferring DNA segments include, for example, the ~1.6 kb BamHI restriction fragment of plasmid pLR2. Other neomycin resistance conferring DNA segments include, for example, the ~3.5 kb PstI restriction fragment and the ~3.4 kb BamHI restriction fragment of plasmid pLR1. Plasmids pLR2 and pLR1 are constructed in accordance with U.S. Pat. No. 4,416,994 and the constructions are incorporated herein by reference.

Additional DNA segments conferring resistance to the above or to different antibiotics such as, for example, hygromycin, chloramphenicol, streptomycin, viomycin, tylosin, erythromycin, and the like can also be constructed and used for purposes of the present invention. Moreover, various functional derivatives of the above described antibiotic resistance conferring DNA segments can be constructed by adding, eliminating, or substituting nucleotides in accordance with the genetic code. Those skilled in the art will understand that ligation of these, or any other antibiotic resistance conferring DNA segments, with cosmid pKC420 DNA, results in cosmid shuttle vectors that are within the scope of the present invention.

The above described cosmid pKC420 and any cosmids derived thereof, as well as the antibiotic resistance conferring DNA segments, can be conveniently modified to facilitate subsequent ligation. For example, the addition of an EcoRI molecular linker with EcoRI-BamHI-EcoRI sites to cosmid pKC427 provides for the construction of a specific restriction site, such as, for example, a BamHI restriction site, that is useful for ligation or for other purposes known in the art. Moreover, the various restriction fragments can also be modified by adding, eliminating, or substituting nucleotides to alter characteristics and to provide a variety of unique or additional restriction sites. Those skilled in the art understand nucleotide chemistry and the genetic code and thus which nucleotides are interchangeable and which DNA modifications are desirable for a specific purpose.

The present vectors are not limited to the use of a specific replicon from an *E. coli* or Streptomyces plasmid. Although the *E. coli* functional replicon exemplified in the present cosmid vectors is from plasmid pBR322, other *E. coli* replicon containing fragments can be obtained from, for example, plasmids pBR324 and pBR325 (disclosed in Bolivar, F., 1978, *Gene* 4:121), plasmid pBR328 (disclosed in Soberon, X., 1980, *Gene* 9:287), pcos2EMBL (Poustka et al., 1984, *Proc. Natl. Acad. Sci. USA* 81:4129), λdv (Little and Cross, 1985, *Proc. Natl. Acad. Sci. USA* 82:3159) i$^{434}$dv (Wold et al., 1982, *Proc. Natl. Acad. Sci. USA* 79:6176), or the like, to produce novel bifunctional cosmids. Additionally, other Streptomyces replicon containing fragments can be substituted for the Streptomyces replicon. These replicon containing fragments include, but are not limited to, replicons from plasmids SCP2 and SCP2* (disclosed in Bibb and Hopwood, 1981, *J. Gen. Microbiol.* 126:427), SLP1 (disclosed in Bibb, M. J., 1981, *Mol. Gen. Genet.* 184: 230), pEL103 (NRRL 12549), pFJ265 (disclosed in Jones, M. D., et al., 1984, *Plasmid* 11:92), pSAM2(Pernodet et al., 1984, *Mol. Gen. Genet.* 198:35) and pHJL210 (NRRL B-15824). Those skilled in the art will understand that ligation of these, or any other *E. coli* or Streptomyces replicon containing fragment, results in cosmid shuttle vectors that are within the scope of the present invention.

The Streptomyces plasmid SCP2* is a high fertility variant of the *S. coelicolor* A3(2) plasmid SCP2 and contains plasmid replication, stability, transfer and fertility functions. The phenotype of an SCP2* derivative, pHJL202 (see Example 6), revealed that plasmid replication and fertility functions are located on an ~12.9 kb EcoRI-BamHI restriction fragment. Since the fertility functions are contained within this DNA fragment, vectors constructed with such fragment can be conjugally transmitted among Streptomyces and related strains. These vectors are particularly advantageous in that they are available for use in a broader host range than the previously described vectors. Cosmid shuttle vectors were constructed to confirm this hypothesis. Thus, the ~12.9 kb EcoRI-BamHI fragment was inserted into cosmid pKC473 to construct cosmid shuttle vector pKC505. *Streptomyces lividans* TK23 (NRRL 15826) was transformed by pKC505 and used as the donor strain in a conjugation with an apramycin sensitive, spectinomycin resistant (Spc$^R$) *S. lividans* strain. Spc$^R$, Am$^R$ exconjugant colonies could be selected.

The recombinant DNA cosmid shuttle vectors of the present invention are not limited for use in a single species or strain of Streptomyces. To the contrary, the vectors are broadly applicable and can be transformed into host cells of many Streptomyces taxa, particularly restrictionless strains of economically important taxa that produce antibiotics such as aminoglycoside, macrolide, β-lactam, polyether, and glycopeptide antibiotics. Such restrictionless strains are readily selected and isolated from Streptomyces taxa by conventional procedures well known in the art. (Lomovskaya et al., 1980, *Microbiological Reviews* 44:206). Host cells of restrictionless strains lack restriction enzymes and therefore do not cut or degrade plasmid DNA upon transformation. For purposes of the present application, host cells containing restriction enzymes that do not cut any of the restriction sites of the present recombinant cosmids are also considered restrictionless.

Preferred host cells of restrictionless strains of Streptomyces taxa that produce aminoglycoside antibiotics and in which the present vectors are especially useful and can be transformed, include restrictionless cells of, for example: *Streptomyces kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma paromomycinus (paromomycins, catenulin), *S. fradiae* var. *italicus* (aminosidine), *S. bluensis* var. bluensis (bluensomycin), *S. catenulae* (catenulin), *S.*

*olivoreticuli* var. cellulophilus (destomycin A), *S. lavendulae* (neomycin), *S. albogriseolus* (neomycins), *S. albus* var. metamycinus (metamycin), *S. hygroscopicus* var. sagamiensis (spectinomycin), *S. bikiniensis* (streptomycin), *S. griseus* (streptomycin), *S. erythrochromogenes* var. narutoensis (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. limoneus (validamycins), *S. rimofaciens* (destomycins), *S. hyqroscopicus* forma globosus (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasuqaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of *Streptomyces taxa* that produce macrolide antibiotics and in which the present vectors are especially useful and can be transformed, include restrictionless cells of, for example: *Streptomyces caelestis* (antibiotic M188), *S. platensis* (platenomycin), *S. rochei* var. volubilis (antibiotic T2636), *S. venezuelae* (methymycins), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S cinerochromoqenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. coilmyceticus (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. espinomyceticus (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. suragaoensis (kujimycins), *S. kitasatoensis* (leucomycin), *S. narbonensis* var. josamyceticus (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of *Streptomyces taxa* that produce β-lactam antibiotics and in which the present vectors are especially useful and can be transformed, include restrictionless cells of, for example: *Streptomyces lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus*, and *S. sioyaensis* (MM 4550 and MM 13902).

Preferred host cells of restrictionless strains of *Streptomyces taxa* that produce polyether antibiotics and in which the present vectors are especially useful and can be transformed, include restrictionless cells of, for example: *Streptomyces albus* (A204, A28695A and B, salinomycin), *S. hygroscopicus* (A218, emericid, DE3936), A120A, A28695A and B, etheromycin, dianemycin), *S. griseus* (grisorixin), *S. conglobatus* (ionomycin), *S. eurocidicus* var. asterocidicus (laidlomycin), *S. lasaliensis* (lasalocid), *S. ribosidificus* (lonomycin), *S. cacaoi* var. asoensis (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of *Streptomyces taxa* that produce glycopeptide antibiotics and in which the present vectors are especially useful and can be transformed, include restrictionless cells of, for example: *Streptomyces orientalis* and *S. haranomachiensis* (vancomycin); *S. candidus* (A-35512, avoparcin), *S. eburosporeus* (LL-AM 374), and *S. toyocaensis* (A47934).

Preferred host cells of other Streptomyces restrictionless strains in which the present vectors are especially useful and can be transformed, include restrictionless cells of, for example: *Streptomyces coelicolor, S. qranuloruber, S. roseosporus, S. lividans, S. griseofuscus, S. acrimycins, S. glaucescens, S. parvilin, S. pristinaespiralis, S. violaceoruber, S. vinaceus, S. virginiae, S. espinosus*, and *S. azureus*.

In addition to the representative Streptomyces host cells described above, the present vectors are also useful and can be transformed into cells of restrictionless strains of other taxa such as, for example: Bacillus, Staphylococcus and related Actinomycetes, including Streptosporangium, Actinoplanes, Nocardia, and Micromonospora. Thus, the vectors of the present invention have wide application and are useful and can be transformed into host cells of a variety of organisms.

While all the embodiments of the present invention are useful, some of the present recombinant DNA cloning vectors and transformants are preferred. Accordingly, preferred vectors are cosmids pKC420, pKC427, pKC428, pKC448, pKC462A, pKC467, cos111, pKC505, and pKC531; and preferred transformants are *Streptomyces ambofaciens*/pKC420, *S. ambofaciens*/pKC427, *S. ambofaciens*/pKC428, *S. ambofaciens*/pKC448, *S. ambofaciens*/pKC462A, *S. ambofaciens*/pKC467, *S. lividans* TK23/cos111, *S. lividans* TK23/pKC505, *S. lividans* TK23/pKC513, *S. lividans* TK23/pKC531, *E. coli* K12 SF8/pKC420, *E. coli* K12 SF8/pKC427, *E. coli* K12 SF8/pKC428, *E. coli* K12 SF8/pKC448, *E. coli* K12 SF8/pKC462A, *E. coli* K12 SF8/pKC467, *E. coli* K12 SF8/cos111, *E. coli* K12 DH1/pKC505, and *E. coli* K12 DH1/pKC531. Moreover, of this preferred group, cosmids pKC420, pKC462A, pKC467, cos111, pKC505, and transformants *S. ambofaciens*/pKC420, *S. ambofaciens*/pKC462A, *S. ambofaciens*/pKC467, *S. lividans* TK23/cos111, *E. coli* K12 SF8/pKC420, *E. coli* K12SF8/pKC462A, *E. coli* K12 SF8/pKC467, *E. coli* K12SF8/cos111, *E. coli* K12 DH1/pKC505, and *E. coli* K12/pKC531 are most preferred.

The recombinant DNA cloning vectors and transformants of the present invention have broad utility and help fill the need for suitable cloning vehicles for use in Streptomyces and related organisms. Moreover, the ability of the present vectors to confer resistance to antibiotics that are toxic to non-transformed host cells, also provides a functional means for selecting transformants. This is important because of the practical necessity for determining and selecting the particular cells that have acquired vector DNA. Additional DNA segments, that lack functional tests for their presence, can also be inserted in the present vectors and then transformants containing the nonselectable DNA can be isolated by appropriate antibiotic selection. Such nonselectable DNA segments can be inserted at any site, except within regions necessary for plasmid function, maintainance, and replication, and include, but are not limited to, genes that specify antibiotic modification enzymes, antibiotic resistance, antibiotic biosynthesis, and regulatory genes of all types.

The present invention further comprises a novel method for using the aforedefined recombinant DNA cosmid shuttle vectors to construct genomic DNA libraries, said method comprising:

(a) ligating a genomic DNA segment into a cosmid shuttle vector, said vector comprising:
  (1) a replicon that is functional in *E. coli*,
  (2) a replicon that is functional in Streptomyces,
  (3) a DNA segment that contains two or more cos sequences of bacteriophage lambda, and
  (4) one or more DNA segments that convey resistance to at least one antibiotic when transformed into a sensitive restrictionless host cell.
(b) packaging said ligated cosmid into bacteriophage lambda particles,
(c) transducing said packaged cosmid into *E. coli*, and
(d) transforming the recombinant cosmid into a Streptomyces host cell.

Figure 2:
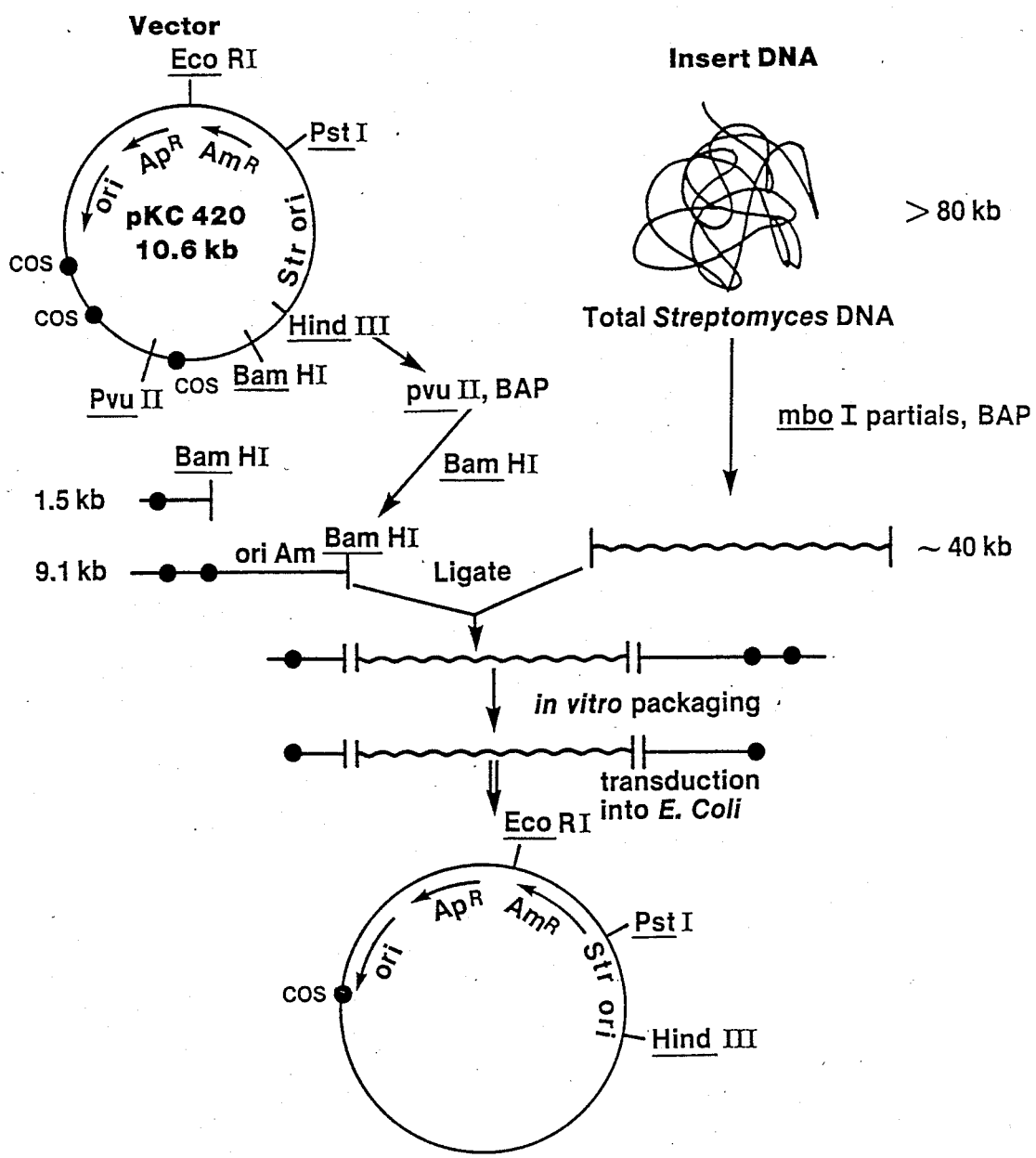
FIG. 2 is a schematic outline of the method of constructing genomic DNA libraries using the cosmid vector pKC420 and Streptomyces DNA.

More particularly and with reference to FIG. 2, cosmid pKC420 DNA was digested with PvuII restriction enzyme to generate a linear fragment with blunt ends. These blunt ends were then dephosphorylated with bacterial alkaline phosphatase (BAP) to prevent their ligation in subsequent reactions. After extraction and precipitation, the DNA was digested with BamHI restriction enzyme to generate two DNA fragments of unequal length, each fragment consisting of a cos site flanked by a reactive BamHI end and a non-reactive PvuII end. The DNA was extracted, precipitated and then involved in DE buffer for subsequent ligation to the insert DNA fragments. Although the preferred embodiment of the method of this invention employs cosmid pKC420, it is apparent that any one of the following cosmids may be used to construct genomic libraries: pKC427, pKC428, pKC448, pKC462, pKC462A, pKC467, cos111, pKC505, pKC513, pKC531, pKC532, and pKC578.

Foreign DNA, such as, for example, *Streptomyces felleus* DNA (NRRL 2251) was partially digested with a restriction enzyme, such as MboI or Sau3A, to generate a size range (average size of 40 kb) of *S. felleus* DNA fragments. These fragments were subsequently treated with BAP to prevent any MboI-generated ends from ligating to each other. Thus, the only allowed ligation was between the MboI ends of the insert DNA and the compatible BamHI ends of the cosmid DNA. The resultant hybrid DNA molecules served as substrates for in vitro packaging of bacteriophage lambda particles. Due to the size selection mechanism of lambda packaging, only those cosmid-insert-DNA molecules in which the cos sequences are 37.8 to 50.9 kb apart were packaged. Since lambda packaging requires two cos sites, one to initiate and another to terminate packaging and is also size selective, large inserts were positively selected for in the transductants. After the desired recombinant DNA procedures were accomplished within the *E. coli* host system, the particular recombinant plasmid DNA was isolated and then transformed into a suitable Streptomyces host.

The method of the present invention enhances both the efficiency and effectiveness of cosmid cloning given the specific construction of these novel cosmid vectors. For example, the presence of two or more cos sites in cosmid pKC420 eliminates the need to separately prepare two cosmid arms. Secondly, digestion of the blunt-end restriction enzyme sites and dephosphorylation of the ends, such as the PvuII and HpaI sites within the multiple cos site region, prevents subsequent cosmid concatemerization between the prepared cosmid arms. Ultimately, given the bifunctionality of the present vectors, the cloned DNA can be shuttled into a Streptomyces host cell for functional analysis of the cloned DNA. This last function is particularly advantageous over known cosmid vehicles as Streptomyces cosmid vectors have yet to be exploited.

*Escherichia coli* K12 DH1/pKC420, as a source of cosmid vector pKC420 (NRRL B-15837) and *E. coli* K12SF8/pKC462A, as a source of cosmid vector pKC462A (NRRL B-15973), can be cultured in a number of ways using any of several different media. Carbohydrate sources which are preferred in a culture medium include, for example, glucose and glycerol, and nitrogen sources include, for example, ammonium salts, amino acid mixtures, and peptones. Nutrient inorganic salts are also incorporated and include the customary salts capable of yielding magnesium, sodium, potassium, ammonia, calcium, phosphate, chloride, sulfate, and like ions. As is necessary for the growth and development of other microorganisms, essential trace elements are also added. Such trace elements are commonly supplied as impurities incidental to the addition of other constituents of the medium.

*E. coli* K12 DH1/pKC420 and *E. coli* K12 SF8/pKC462A were grown under aerobic culture conditions over a relatively wide pH range of about 6.5 to 7.4 at temperatures ranging from about 30° to 42° C. For the production of the cosmid vectors pKC420 and pKC462A in the greatest quantity, however, it is desirable to start with a culture medium at a pH of about 7.4 and maintain a culture temperature of about 30° C. Culturing the *E. coli* cells under the aforementioned conditions resulted in a reservoir of cells from which cosmids pKC420 and pKC462A were isolated by techniques well known in the art.

The following examples further illustrate and detail the invention disclosed herein. Both an explanation of and the actual procedures for constructing the invention are described where appropriate.

EXAMPLE 1

Culture of *E. coli* K12 DHI/pKC420 and Isolation of Cosmid pKC420

A. Culture 5 ml. cultures of *E. coli* K12 DH1/pKC420 (NRRL B-15837) were grown under selective conditions in TY media (1% tryptone, 0.5% yeast extract, 0.5% sodium chloride, pH 7.4) according to conventional microbiological procedures. The cells were spun in a table top centrifuge and the pellet resuspended in 1 ml. of 0.3M sucrose, 25 mM EDTA (ethylene diaminetetracetate) and 25 mM Tris-HCl pH 8 (Solution I). After transfer to an Eppendorf tube the cells were centrifuged for about one minute and the pellet was resuspended in 0.5 ml. of Solution I. About 50 μl. of freshly made lysozyme (20 mg./ml. in water) was added and the solution was incubated for 10 minutes at 37° C.

After the addition of 250 μl. of freshly made lysis mix (2% sodium dodecyl sulfate and 0.3N NaOH), the cells were immediately and completely vortexed. The cells were then incubated for ten minutes at 50° C., cooled. To this 100 μl. of phenol-Sevag (phenolchloroform-isoamyl alcohol, 25-24-1) was added and vortexed. After the DNA was centrifuged for two minutes in an Eppendorf centrifuge, the supernatant was transferred to another tube with 70 μl. of unbuffered 3M sodium acetate and 0.7 ml of isopropanol to precipitate the DNA. This solution was incubated for five minutes at room temperature and then centrifuged for five minutes. The supernatant was completely removed including the excess liquid sticking to the wall of the centrifuged tube.

The DNA precipitate was redissolved in 500 μl. of TE (10 mM Tris-HCl pH 8 and 1 mM EDTA) and 10 μl. of 100 mM Spermine HCl was added. This mixture was vortexed and then incubated for five minutes at room temperature before a five minute spin in an Eppendorf centrifuge. The supernatant was completely removed and the precipitated DNA was vortexed with 1 ml. of 75% ethanol, 0.3M sodium acetate, and 10 mM magnesium acetate. This solution was incubated for five minutes at room temperature and the DNA collected as above. The pellet was redissolved in 10 μl. of TE for subsequent use as a cloning vehicle.

EXAMPLE 2

Construction of Cosmid Shuttle Vector pKC427

A BamHI Digestion of Cosmid pKC420

About 5 82 g. of cosmid pKC420 were digested in 1X BamHI buffer (150 mM NaCl, 6 mM Tris-HCl pH 7.9, 6 mM MgCl$_2$ and 1 mM Dithiothreitol) in a total volume of 50 μl. with 20 units (New England Biolab) of BamHI restriction endonuclease*. The mixture was incubated at 37° C. for about 1 hour and then the reaction was terminated by incubation at 70° C. for 10 minutes. Since cosmid pKC420 has a single BamHI site, digestion is easily monitored by agarose gel electrophoresis. The appearance of a single band of about 10 kb signals complete digestion. The DNA was extracted with phenol and Sevag (chloroform:isoamylalcohol 24:1), precipitated with ethanol, the precipitate was collected by centrifugation, dried and then resuspended in TE for subsequent ligation.
*Restriction enzymes and instructions can be obtained from the following sources:
New England BioLabs., Inc., 32 Tozer Road, Beverly, Mass., 01915
Bethesda Research Laboratories, Inc., P.O. Box 577, Gaithersburg, Me., 20760
Boehringer-Mannheim Biochemicals, P.O. Box 50816, Indianapolis, Ind., 46250

B. BclI Digestion of Plasmid pIJ702

About 5 μg. of plasmid pIJ702 DNA (ATCC 39155) were digested in 1X BclI buffer (75 mM KCl, 6 mM Tris-HCl pH 7.4, 10 mM MgCl$_2$ and 1 mM Dithiothreitol) in a total volume of 50 μl. with 10 units (New England Biolab) of BclI restriction endonuclease. The mixture was incubated at 50° C. for about an hour and then the reaction was terminated by extraction with phenol and Sevag, precipitated with ethanol, dried and then dissolved in 5 μl. TE. The DNA was electrophoresed on a 0.5% agarose gel until the desired ~1 kb BclI fragment was separated from other fragments. Whatman DEAE cellulose paper was placed in a slit prepared ahead of the desired DNA band and the DNA was electrophoresed onto the DEAE paper. The paper was washed with 1 ml. of TE and the DNA was eluted with 400 μl. of TE adjusted to 1M by the addition of an appropriate volume of NaCl. The eluted DNA was ethanol precipitated and finally dissolved in 5 μl. of TE.

C Ligation and Construction of E. coli K12 SF8/pKC427

Figure 3:
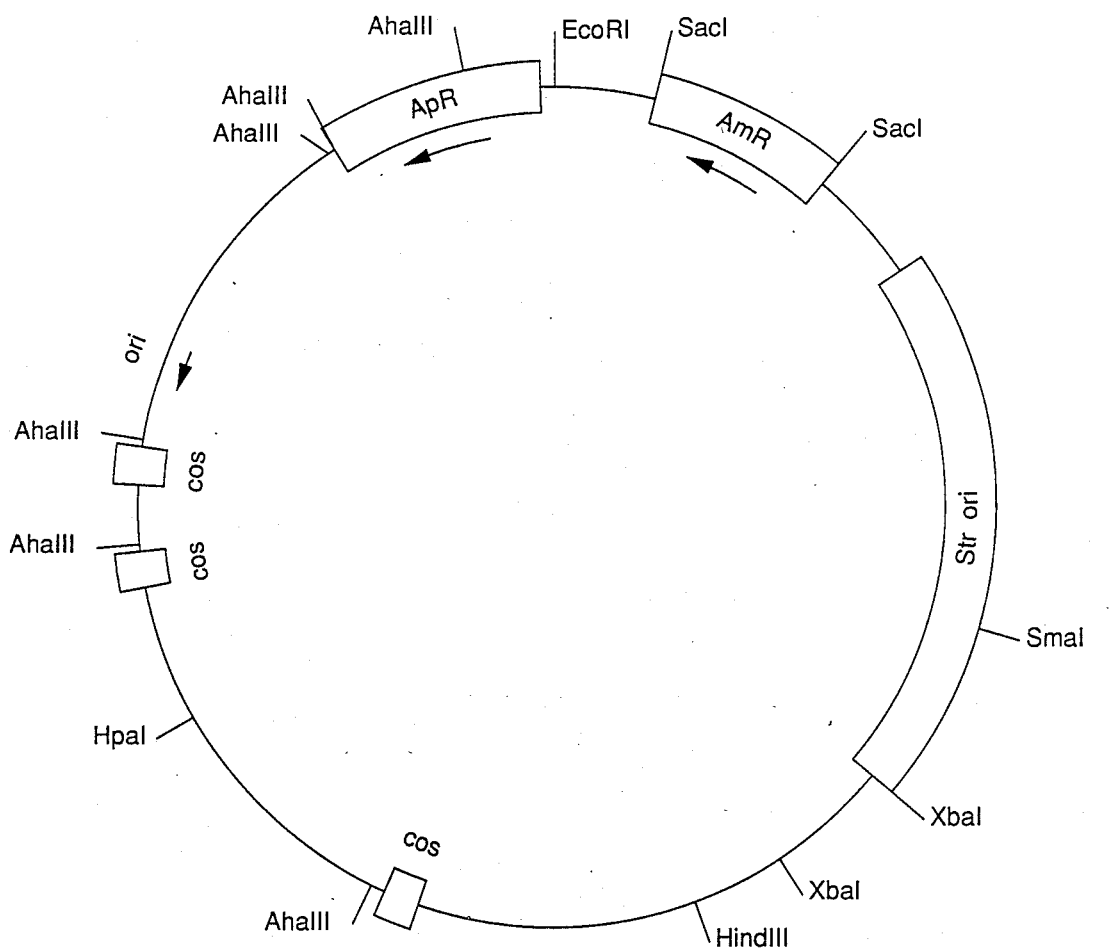
FIG. 3 is a restriction site and function map of cosmid pKC427.

About 1 μg. each of BamHI-digested cosmid pKC420 DNA and the ~1 kb BclI thiostrepton resistance conferring fragment were ligated in 20 μl. of 1X ligase buffer (50 mM Tris-HCl pH 7.8, 10 mM MgCl$_2$, 20 mM Dithiothreitol and 1 mM ATP) with 400 units of T4 DNA ligase* for 16 hours at 16° C. The reaction was terminated by incubation at 70° C. for 10 minutes. After cooling on ice, the resultant ligated DNA was used to transform E. coli K12 SF8 (NRRL B-15835) according to the procedure of Maniatis et al., 1982, Molecular Cloning, Cold Spring Harbor Laboratory, Cold Spring Harbor, N.Y. The identity of the desired transformants was conventionally confirmed by screening for the loss of the BamHI site and the acquisition of a SalI site. Competent cells were stored in 20% glycerol, instead of dimethyl sulfoxide, at −70° C. The resultant E. coli K12 SF8/pKC427 transformants were conventionally cultured for subsequent production and isolation of cosmid pKC427. A restriction site and function map of cosmid pKC427 is presented in FIG. 3 of the accompanying drawings.
*T4 DNA ligase can be obtained from the same sources as those identified for restriction enzymes.

EXAMPLE 3

Construction of Cosmid Shuttle Vector pKC428

A. EcoRI Digestion of Cosmid pKC427

About 5 μg. of cosmid pKC427 DNA were digested in 1X EcoRI buffer (50 mM NaCl, 100 mM Tris-HCl pH 7.5, 5 mM MgCl$_2$ and 1 mM Dithiothreitol) in a total volume of 50 μl. with 20 units (New England Biolab) of EcoRI restriction endonuclease. The mixture was incubated at 37° C. for about 1 hour and then the reaction was terminated by incubation at 70° C. for 10 minutes. Since cosmid pKC427 contains a unique EcoRI site, an EcoRI digestion generates a single linear fragment.

B. EcoRI Digestion of Plasmid pUC4K and Isolation of the ~1.5 kb EcoRI Neomycin Resistance-Conferring Gene The desired digestion was carried out in substantial accordance with the teaching of Example 3A except that plasmid pUC4K (NRRL B-15836) DNA, rather than cosmid pKC427 DNA, was used. The isolation of the ~1.5 kb EcoRI fragment was carried out in substantial accordance with the teaching of Example 2B.

C. Ligation and Construction of E. coli K12 SF8/pKC428

Figure 4:
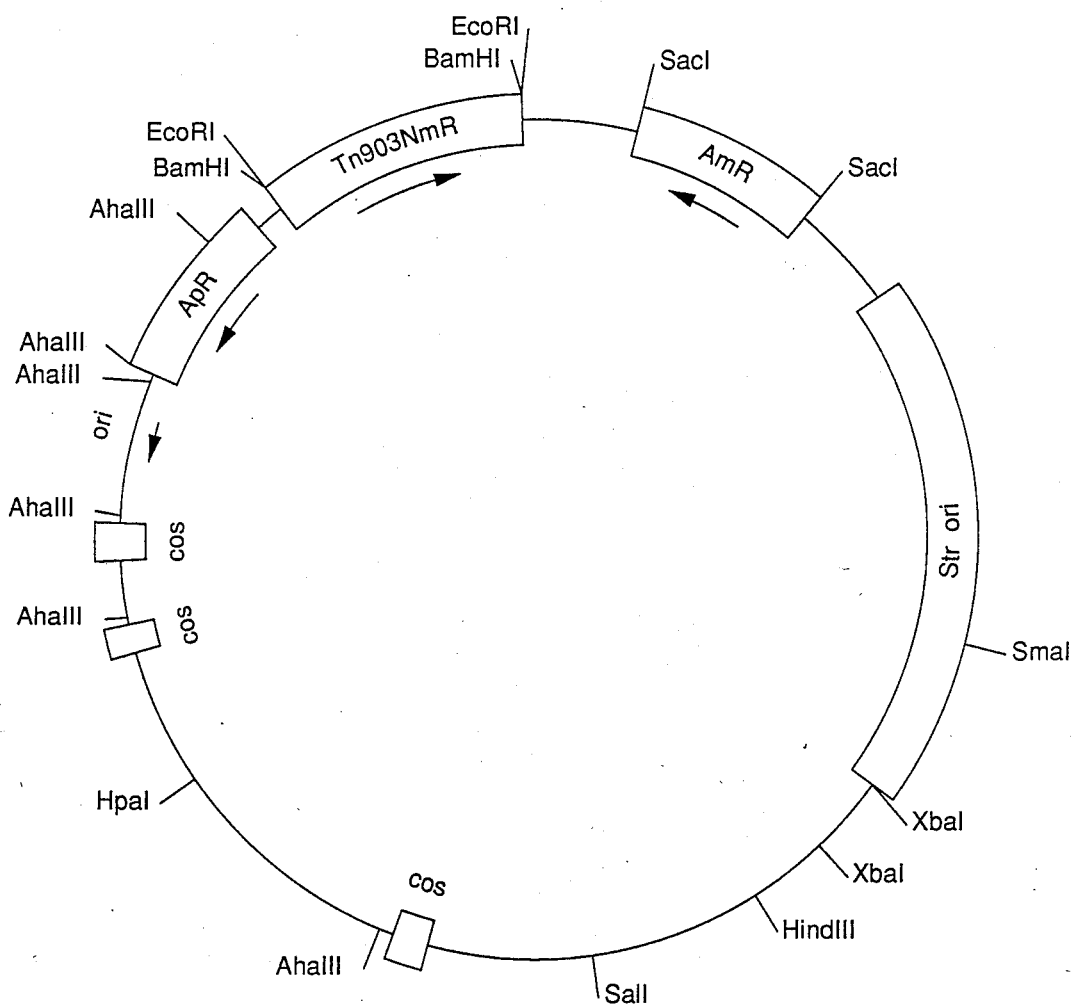
FIG. 4 is a restriction site and function map of cosmid pKC428.

The ligation and subsequent transformation procedures were carried out in substantial accordance with the teaching of Example 2C. The identity of the desired transformants was conventionally confirmed by initially selecting for Am$^R$ phenotype and then replicating those Am$^R$ colonies to select for neomycin resistant colonies. These colonies were additionally screened for the acquisition of BamHI and SalI restriction sites. A restriction site and function map of cosmid pKC428 is presented in FIG. 4 of the accompanying drawings.

EXAMPLE 4

Construction of Cosmid Shuttle Vector pKC448

A. BamHI Digestion of Cosmid pKC428 and Subsequent Ligation

Figure 5:
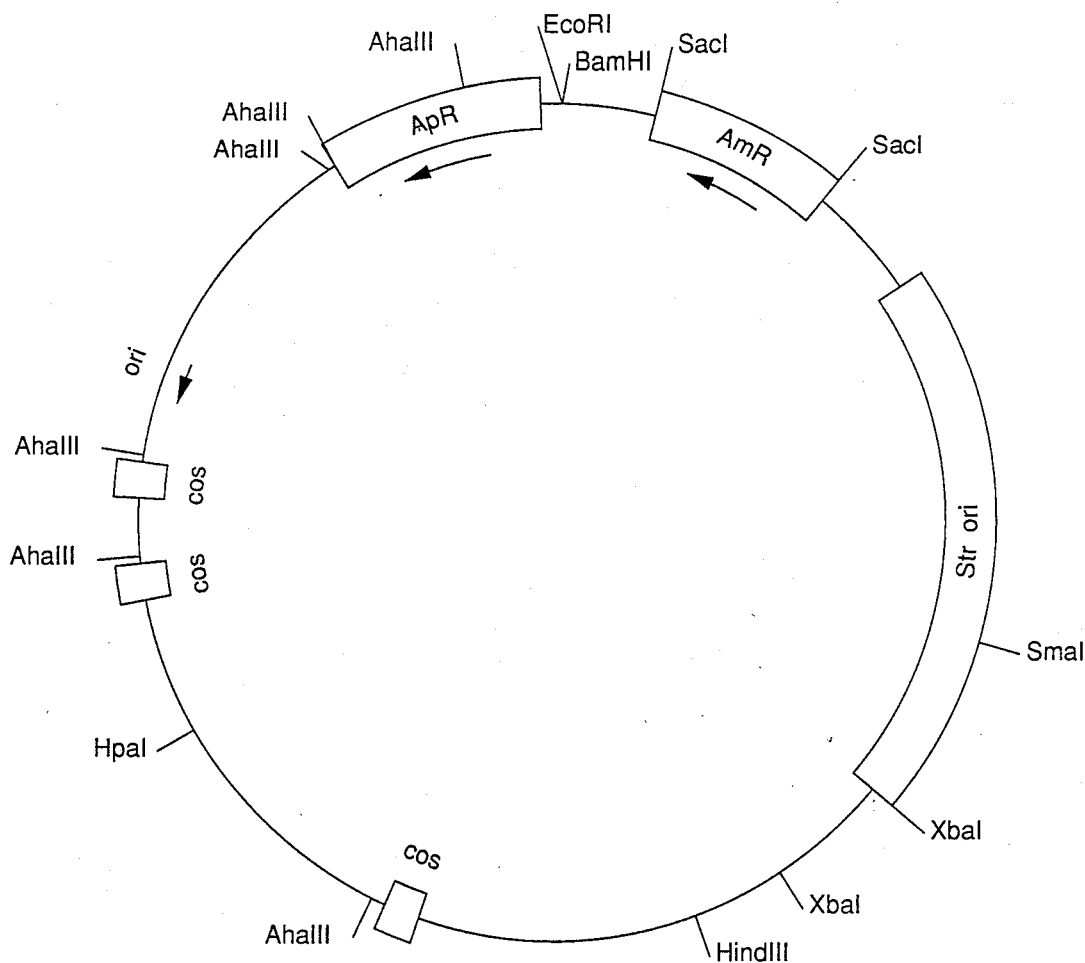
FIG. 5 is a restriction site and function map of cosmid pKC448.

Cosmid pKC448 was constructed by deleting a BamHI fragment from cosmid pKC428. The desired BamHI digestion was carried out in substantial accordance with the teaching of Example 2A except that cosmid pKC428 DNA was used in place of cosmid pKC420 DNA. The resulting fragments were recovered and self-ligated in substantial accordance with the teaching of Examples 2B and 2C. This digestion results in the removal of the neomycin resistance conferring gene and generates a unique BamHI site flanked by two EcoRI sites. A restriction site and function map of cosmid pKC448 is presented in FIG. 5 of the accompanying drawings.

EXAMPLE 5

Construction of Cosmid pKC462

A. HindIII and SalI Digestion of Cosmid pKC448

About 10 µg. of cosmid pKC448 were digested in 100 µl. of buffer (150 mM NaCl, 6 mM Tris-HCl pH 7.9, 6 mM MgCl$_2$ and 1 mM Dithiothreitol) with 20 units each of HindIII and SalI restriction enzymes for 2 hours at 37° C. The DNA was ethanol precipitated and then resuspended in 20 µl. of TE.

B. Digestion of Plasmid pKC7 DNA and Isolation of the Neomycin Resistance-Conferring Gene The desired digestion of the ~1.5 kb HindIII-SalI fragment is carried out in substantial accordance with the teaching of Example 5A except that plasmid pKC7 (ATCC 37084) is used in place of cosmid pKC448.

C. Ligation and Construction of E. coli DH1/pKC462

Figure 6:
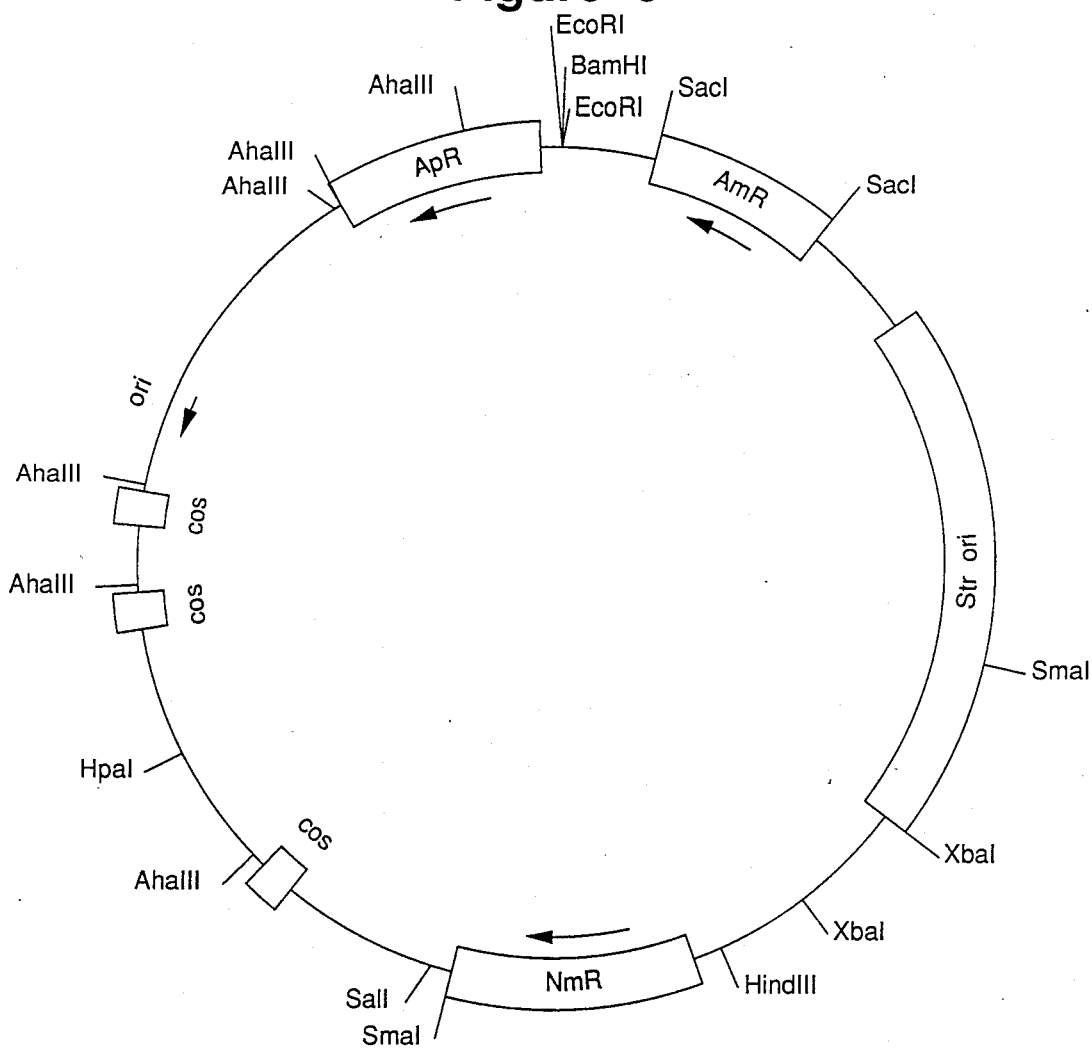
FIG. 6 is a restriction site and function map of cosmid pKC462.

The ligation and subsequent transformation procedures were carried out in substantial accordance with the teaching of Example 2C except that E. coli DH1 (NRRL B-15021) was used in place of E. coli K12 SF8. In addition, cosmid pKC462 DNA was used in place of cosmid pKC427 DNA. The identity of the desired transformants was conventionally confirmed by initially selecting for Am$^R$ phenotype and then replicating those Am$^R$ colonies to select for neomycin resistant colonies. A restriction site and function map of cosmid pKC462 is presented in FIG. 6 of the accompanying drawings.

EXAMPLE 6

Construction of E. coli K12 SF8/pKC448

The desired construction was made, selected, and recovered in substantial accordance with the teaching of Example 2C except that cosmid pKC448 DNA was used in place of cosmid pKC427 DNA. The identified transformants were then used for subsequent production and isolation of cosmid pKC448 according to the teaching of Example 1.

EXAMPLE 7

Construction of Streptomyces ambofaciens/pKC420 and S. ambofaciens/pKC448

About 1 µg. each of the DNA from Examples 1 and 3 and 200 µl. of protoplasts of Streptomyces ambofaciens, a strain deposited and made part of the permanent stock culture collection of the Northern Regional Research Laboratories, Peoria, Ill., from which it is available to the public under the accession number NRRL 2420, were mixed with 500 µl. of 55% polyethylene glycol (Sigma) in P medium (Hopwood and Wright, 1978, *Molecular and General Genetics* 162:307), vortexed, and then aliquots of 25 µl. and 250 µl. were plated onto R2YE* plates with 3 ml. of R2YE top agar. The plates were incubated for 18 hours at 30° C. and then overlayed with 3 ml. of R2YE top agar containing sufficient apramycin** for a final concentration of 50 µg./ml. The plates were then incubated for an additional 3 days at 30° C. The resultant S. ambofaciens/pKC420 and S. ambofaciens/pKC448 apramycin resistant colonies were isolated according to known procedures, cultured, and then conventionally identified by back transformation into other Streptomyces species.

*R2YE medium was prepared with the following composition per liter: Sucrose-103 g. 2.5% K$_2$SO$_4$-10 ml. MgCl$_2$-10.1 g. Glucose-10 g. Casamino acids-0.1 g. Agar-22 g. Trace Element Mix-2 ml. 0.5% KH$_2$PO$_4$-10 ml. 1M CaCl$_2$-20 ml. Proline-3 g. 0.25M TES pH 7.2-100 ml. 10% Yeast extract-50 ml.
**Antibiotic apramycin can be obtained from either Sigma, St. Louis, Mo., or Eli Lilly and Company, Indianapolis, Ind.

EXAMPLE 8

The Construction of a Genomic Library

A. Preparation of the Vector pKC420 DNA

About 50 µg. of cosmid pKC420 DNA were digested in 500 µl. of 1X PvuII (60 mM NaCl, 6 mM Tris-HCl pH 7.5, 6 mM MgCl$_2$ and 1 mM Dithiothreitol) buffer with 100 units of PvuII restriction enzyme for 3 hours at 37° C. About 50 µl. of 10X BAP buffer (500 mM Tris-HCl pH 8 and 500 mM NaCl) and 2.5 units of BAP (International Biotechnologies, Inc., P.O. Box 1565, New Haven, Conn. 06506) were added and incubated for 1 hour at 70° C. The DNA was extracted with phenol, Sevag and precipitated with ethanol. The DNA was then digested in 500 µl. of 1X BamHI buffer with 90 units of BamHI restriction enzyme for 3 hours at 37° C. The DNA was again extracted with phenol, Sevag, precipitated with ethanol and finally dissolved in 50 µl. of TE.

B. Preparation of the Insert DNA

*Streptomyces felleus* (NRRL 2251) was grown in 250 ml. of Tryptic Soy broth (TSB) supplemented with 100 µg./ml. of spiramycin* for 16 hours at 30° C. The cells were harvested by centrifugation (10 minutes at 8,000 rpm), suspended in 10 ml. of lysis mix (300 mM Sucrose, 25 mM Tris-HCl pH 8, and 25 mM EDTA) and brought to a final concentration of 1 mg./ml. with lysozyme and incubated at 37° C. for 10 minutes. Then proteinase K was added to a final concentration of 200 µg./ml. and SDS (sodium dodecyl sulfate) was added to a final concentration of 2%. The mixture was incubated at 70° C. for 10 minutes and then cooled on ice. The mixture was made 1M in potassium acetate and left on ice for 30 minutes. After gently extracting the material with TE saturated phenol, the layers were separated and the aqueous layer was gently extracted with Sevag. Layers were again separated and the nucleic acids in the aqueous layer were precipitated with ethanol. The precipitate was washed with 70% ethanol and then dissolved in 5 ml. TE. RNase A was added to the DNA solution to a final concentration of 50 μg./ml. This solution was then incubated at 37° C. for 30 minutes, extracted twice with phenol, twice with Sevag and then precipitated with ethanol. The DNA was redissolved in 1 ml. TE (545 μg./ml.) and then sized on a 0.3% agarose gel with λ standards and was found to have an average size of 70 kb.

Next, 50 μg. of *Streptomyces felleus* chromosomal DNA were incubated with 30 units of MboI in 500 μl. of 1X MboI buffer (100 mM NaCl, 10 mM Tris-HCl pH 7.4, 10 mM MgCl₂, and 1 mM DTT) at 37° C. for 15 minutes. This particular condition was found, empirically, to give the desired partial fragmentation of chromosomal DNA. The DNA was extracted with phenol, Sevag and then dissolved in 50 μl. of TE.

About 25 μg. of *Streptomyces felleus* MboI partials were subsequently treated with BAP (1.25 units for the first 1 hour at 70° C., and then an additional 1.25 units for another hour at 70° C.) in 100 μl. of 1X BAP buffer. The DNA was extracted with phenol, Sevag, precipitated with ethanol and then dissolved in 50 μl. of TE. The size of this DNA was estimated on a 0.3% agarose gel and was found to be 30-40 kb.

*Antibiotic spiramycin can be obtained from Sigma, St. Louis, Mo.

C. Ligation of the Vector DNA to the Insert DNA

About 125 ng. of pKC420 arms (prepared in Example 8A) were mixed with 500 ng. of *Streptomyces felleus* MboI partials (prepared in Example 8B) and ligated with 400 units (New England Biolabs) of T4 DNA ligase in 20 μl. of 1X ligase buffer made 1 mM in ATP. Ligation was performed for 16 hours at 16° C. and then terminated by heating for 10 minutes at 70° C.

D. In Vitro Packaging

Packaging was performed by adding about 10 μl. of the ligation mixture (~62.5 ng. of hybrid vector DNA) to Biotec packaging kit* at 30° C. for 1 hour. To this mixture, about 500 μl. of 0.1M NaCl, 0.01M Tris-HCl pH 8, and 0.01M MgSO₄ were added. Lastly, 25 μl. of chloroform were added to kill any living bacteria.

*Promega Biotec, 2800 S. Fish Hatchery Road, Madison, Wis. 53711.

E. Transduction of *E. coli* K12 SF8

About 200 μl. of packaged cosmids (25 ng. of vector DNA) were adsorbed to 500 μl. of *E. coli* strain K12 SF8 grown in Tryptone yeast extract supplemented with 0.2% maltose and 10 mM magnesium sulfate. Adsorption was done for 10 minutes at 37° C. in 10 mM Tris pH 8.0 and 10 mM MgSO₄. The cells were grown in 5 ml. of Tryptone yeast extract for three hours at room temperature and transductants were selected at 30° C. on plates supplemented with 200 μg./ml. of apramycin. Approximately 400 colonies resulted from the plating of 0.1 ml. of transduced cells giving rise to a transducing efficiency of about $1.2 \times 10^6$ transductants per microgram.

F. Transformation into Streptomyces ambofaciens

The desired transformation was performed in substantial accordance with the teaching of Example 7. About $3.4 \times 10^4$ transformants per 1 μg. of *E. coli* grown pKC420 were obtained in this experiment.

EXAMPLE 9

Construction of Cosmid pKC467

A. XbaI Digestion of Cosmid pKC462

About 25 μg. of cosmid pKC462 are digested with 200 units of XbaI restriction enzyme in 100 μl. of 1X XbaI buffer (50 mM NaCl, 100 mM Tris-HCl pH 7.5, 5 mM MgCl₂ and 1 mM Dithiothreitol). The mixture is incubated at 37° C. for about 1 hour and then the reaction is terminated by incubation at 70° C. for 10 minutes. The digested DNA is electrophoresed on a 0.5% agarose gel (International Biotech, Inc.) and then the large fragment is isolated on DEAE paper. The isolated DNA is eluted with 400 μl. TE and 1M NaCl and then ethanol precipitated. The DNA is resuspended in 20 μl. TE for subsequent ligation.

B. Ligation and Construction of *E. coli* K12 SF8/pKC467

About 3 μl. (~1.5 μg.) of the isolated DNA are self-ligated and used to transform *E. coli* K12 SF8 in substantial accordance with the teaching of Example 2C. The identity of the desired transformants is conventionally confirmed by initially selecting for Am^R phenotype and then screening the plasmids for the presence of a unique XbaI site. One desired transformant is conventionally cultured for subsequent production and isolation of cosmid pKC467.

Figure 7:
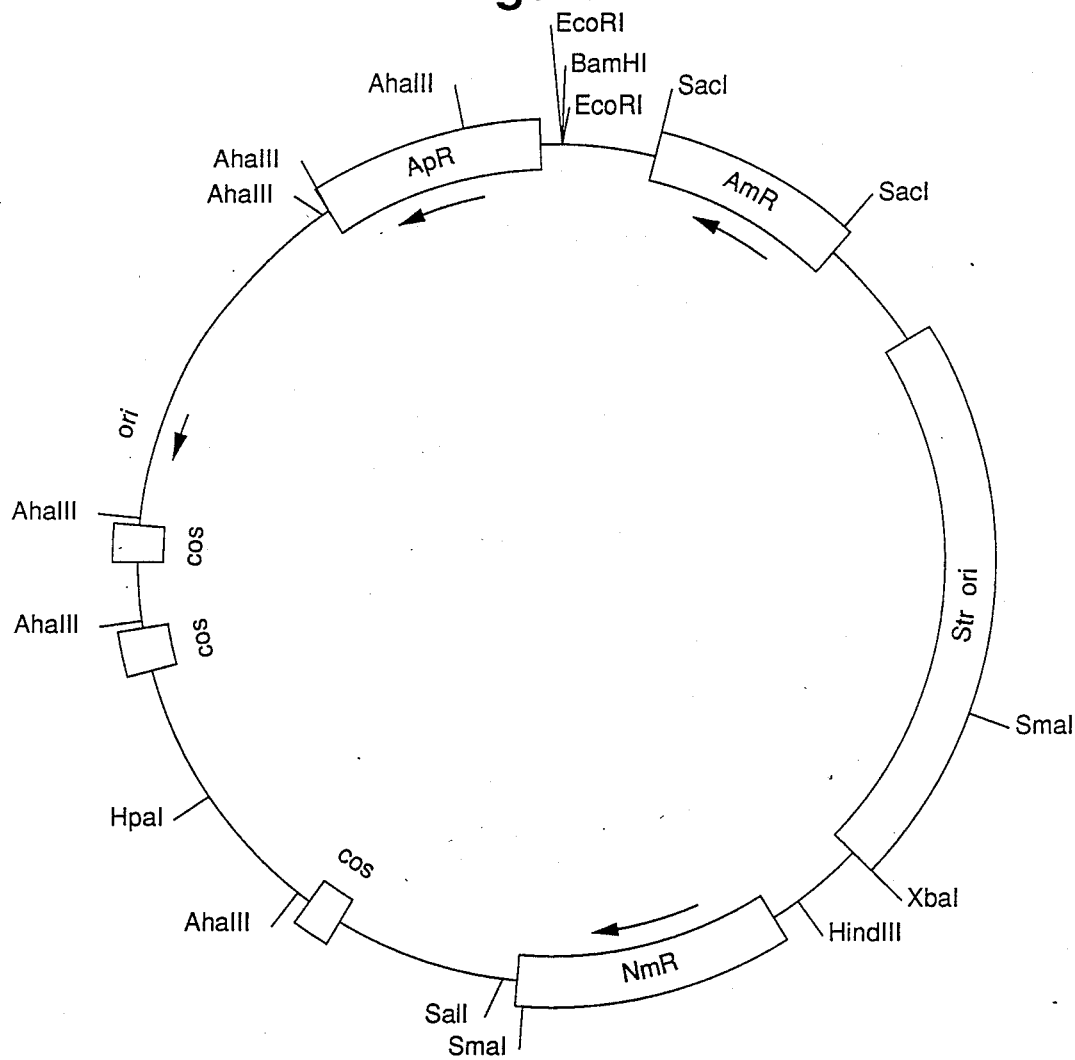
FIG. 7 is a restriction site and function map of cosmid pKC467.

This XbaI deletion results in the generation of a low-copy number Streptomyces vector. Low-copy number vectors are advantageous in that recipient host strains are not likely to be damaged by possible highlevel expression of physiologically active gene products. A restriction site and function map of cosmid pKC467 is presented in FIG. 7 of the accompanying drawings.

EXAMPLE 10

Construction of Streptomyces ambofaciens/pKC462 and *S. ambofaciens*/pKC467

About 1 μg. of DNA from Example 5 and 200 μl. of protoplasts of *Streptomyces ambofaciens* (NRRL 2420) were mixed in substantial accordance with the teaching of Example 7. The identity of the desired transformants was conventionally confirmed by initially selecting for Am^R phenotype and then replicating those Am^R colonies to select for neomycin resistant colonies. The resultant *S. ambofaciens*/pKC462 apramycin resistant and neomycin resistant colonies were isolated according to the teaching of Example 7.

*Streptomyces ambofaciens*/pKC467 can be constructed as taught above by substituting the pKC467 DNA from Example 9 for the pKC462 DNA.

EXAMPLE 11

Culture of *E. coli* K12 SF8/pKC462A and Isolation of Cosmid pKC462A

Figure 8:
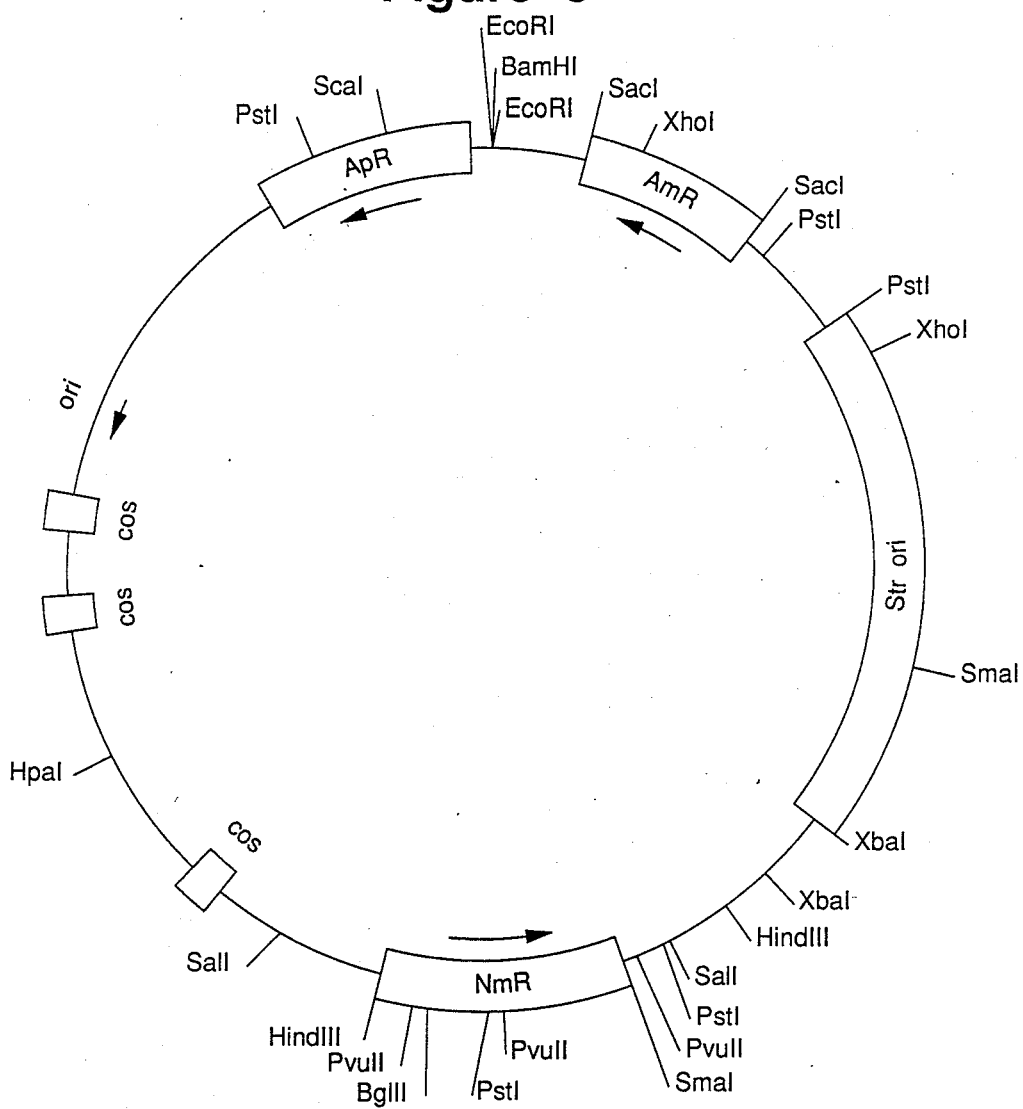
FIG. 8 is a restriction site and function map of cosmid pKC462A.

The culture of *E. coli* K12 SF8/pKC462A (NRRL B-15973) and subsequent isolation of cosmid pKC462A were carried out in substantial accordance with the teaching of Example 1. The ~5 μg of cosmid pKC462A DNA obtained by this procedure was suspended in 1 ml of TE buffer and stored at −20° C. A restriction site and function map of cosmid pKC462A is presented in FIG. 8 of the accompanying drawings. Cosmid pKC462A can be easily distinguished from cosmid pKC462 on the basis of size, as cosmid pKC462A contains approximately 0.9 kb more DNA than cosmid pKC462.

EXAMPLE 12

Construction of Cosmid pKC467A and E. coli K12 SF8/pKC467A

The construction of this low copy number Streptomyces vector is performed in substantial accordance with the teaching of Example 9A except that cosmid pKC462A DNA is substituted for the pKC462 DNA.

E. coli K12 SF8 is transformed with cosmid pKC467A DNA in substantial accordance with the teaching of Example 2C. The identity of the desired transformants can be conventionally confirmed by initially selecting for $Am^R$ phenotype and then screening the plasmids for the presence of a unique XbaI site. One desired transformant is cultured for subsequent production and isolation of cosmid pKC467A. The resultant E. coli K12 SF8/pKC467 transformants are conventionally cultured for subsequent production and isolation of cosmid pKC467A.

EXAMPLE 13

Construction of Streptomyces ambofaciens/pKC462A and S. ambofaciens/pKC467A

About 1 μg of the DNA from Example 11 and 200 μl of protoplasts of Streptomyces ambofaciens (NRRL 2420) were individually mixed in substantial accordance with the teaching of Example 7. The identity of the desired transformants was conventionally confirmed by initially selecting for $Am^R$ phenotype and then analysing the plasmid DNA from the transformants.

Streptomyces ambofaciens/pKC467A can be constructed as taught above by substituting the pKC467A DNA from Example 12 for the pKC462A DNA.

EXAMPLE 14

Construction of Cosmid cos111

A. Construction of Intermediate Plasmid pOJ107

About 25 μg of cosmid pKC462A DNA were digested in 0.5 ml of 1X buffer (150 mM NaCl, 6 mM TrisHCl pH 7.9, 6 mM $MgCl_2$ and 1 mM Dithiothreitol) with 20 units of PstI restriction enzyme for 3 hours at 37° C. The DNA was ethanol precipitated and collected by centrifugation. After the DNA pellet was resuspended in 100 μl of TE, the PstI-digested DNA was electrophoresed on a 0.7% agarose mini gel and isolated by electrolution, using an IBI electrolution apparatus. The ~2.0 kb PstI fragment was isolated by running the gel at 150 V for 30 minutes, followed by ethanol precipitation and resuspension in 50 μl of TE. About 1 μl of this DNA was digested with 20 units BamHI restriction enzyme at 37° C. for 1 hour. The BamHI-PstI-digested DNA was then electrophoresed on a 0.7% agarose gel, and the desired ~1.3 kb BamHI-PstI restriction fragment, containing the apramycin resistance gene, was isolated and purified in substantial accordance with the teaching of Example 2B.

Plasmid pUC19 (commercially available from Pharmacia, Inc., 800 Centennial Dr., Piscataway, N.J. 08854) was similarly treated as taught above with BamHI and PstI restriction enzymes and the BamHI-PstI cut plasmid was ligated to the ~1.3 kb BamHI-PstI fragment of cosmid pKC462A and transformed into E. coli K12 SF8 in substantial accordance with the teaching of Example 2C.

The desired transformants, E. coli K12 SF8/pOJ107, were identified by restriction enzyme analysis of their plasmid DNA and by their apramycinresistant phenotype.

B. Construction of Intermediate Plasmid pOJ108

About 10 μg of plasmid pOJ107 DNA were digested in 20 μl of 1X EcoRI buffer with 20 units of EcoRI restriction enzyme. After precipitation with ethanol, these fragments were resuspended in 100 μl of NdeI buffer with 3 units NdeI restriction enzyme. The plasmid DNA mixture was incubated at 37° C. for 2 hours and then the DNA was ethanol precipitated, collected by centrifugation, and dissolved in 20 μl of TE. Among the fragments generated by this double digestion is the desired EcoRI-NdeI fragment containing the E. coli replicon and both the ampicillin and apramycin resistance conferring genes.

Figure 9:
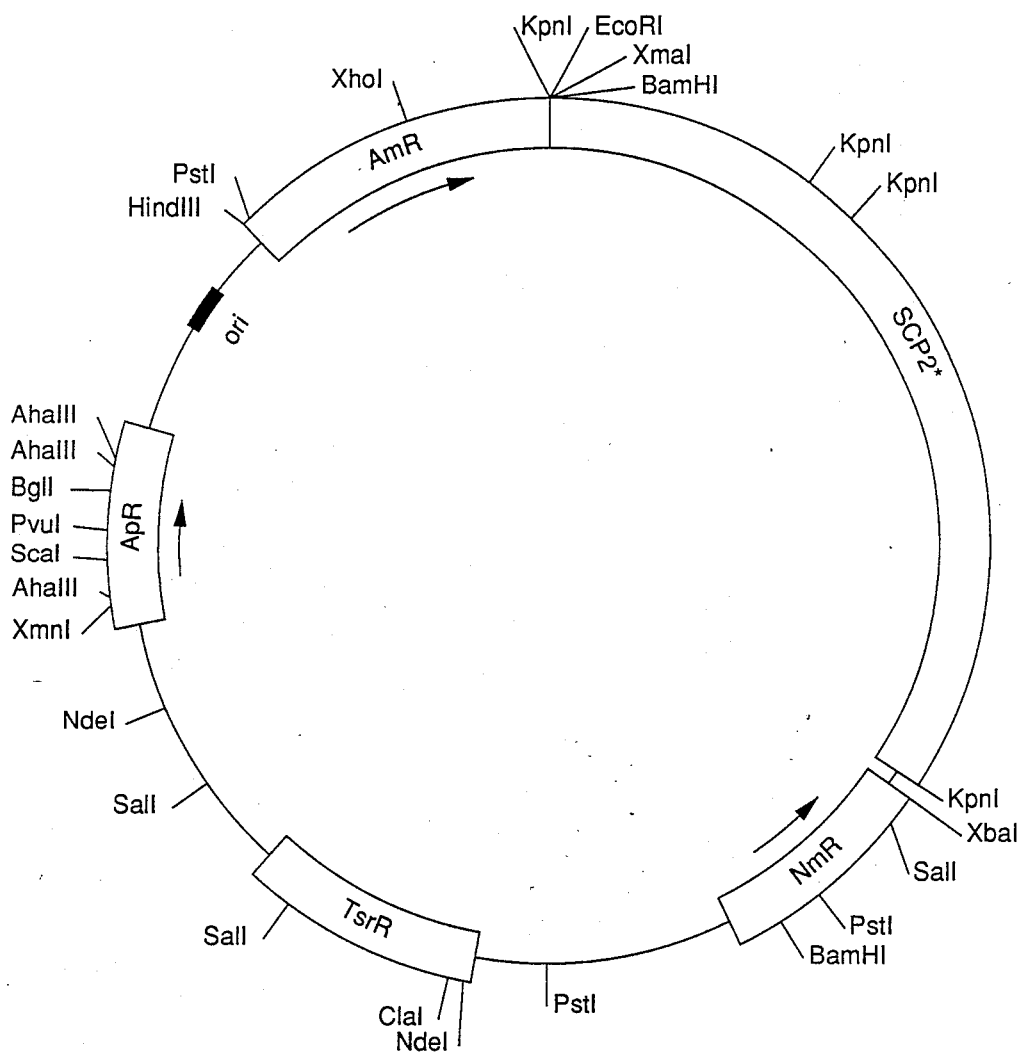
FIG. 9 is a restriction site and function map of plasmid pOJ108.

Partial NdeI restriction enzyme digests were performed on plasmid pHJL210 DNA (NRRL B-15824) by incubating the EcoRI digested pHJL210 DNA at 37° C. for 8 minutes with 3 units of NdeI restriction enzyme. After precipitation, these fragments were cut to completion with 20 units of EcoRI restriction enzyme at 37° C. for 2 hours. The DNA was ethanol precipitated and resuspended in 10 μl of TE. This double digest generated the desired EcoRI-NdeI fragment containing the SCP2* replicon and both the neomycin and thiostrepton resistance-conferring genes. These two plasmid digests were ligated and used to transform E. coli K12 SF8. The resulting transformants, E. coli K12 SF8/pOJ108, were identified by restriction enzyme analysis of their plasmid DNA and by their apramycin-resistant phenotype. A restriction site and function map of plasmid pOJ108 is presented in FIG. 9 of the accompanying drawings.

C. Construction of Intermediate Plasmid pOJ111

Figure 10:
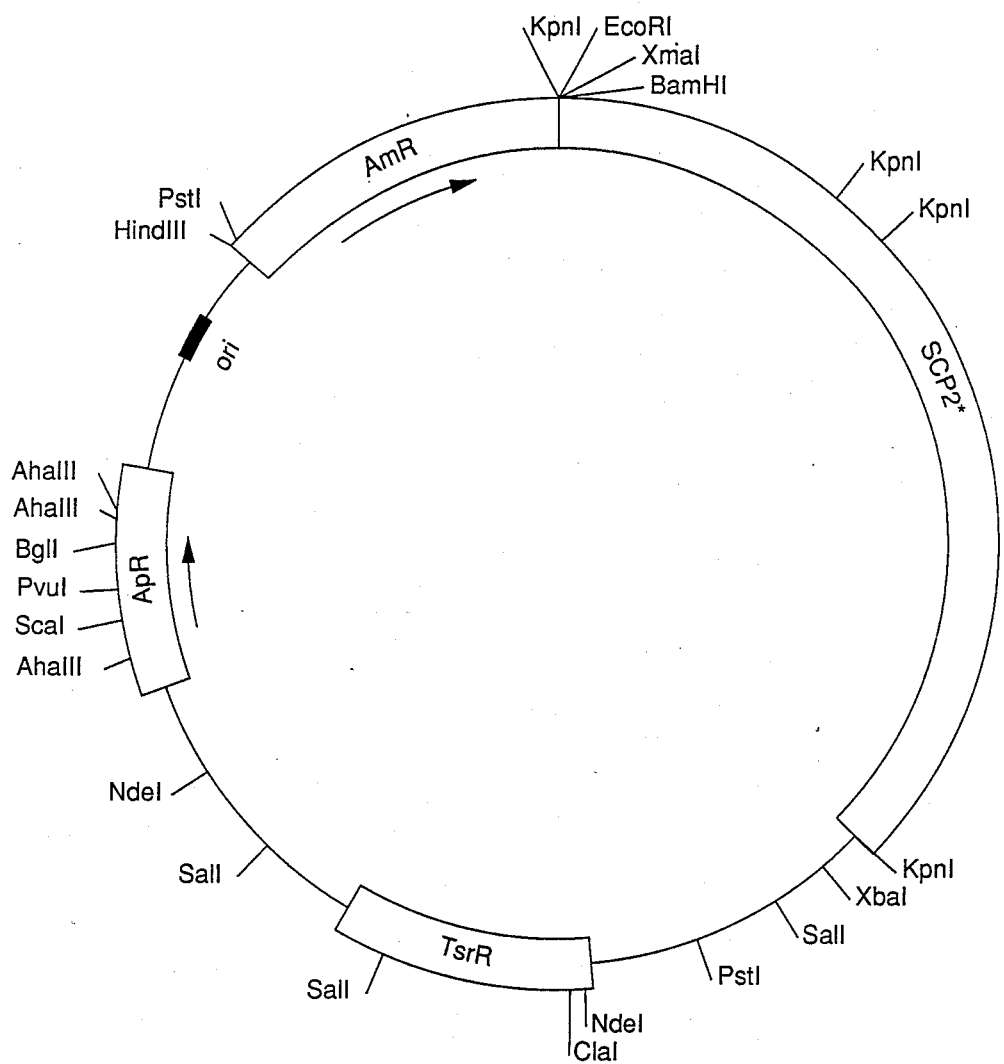
FIG. 10 is a restriction site and function map of plasmid pOJ111.

Ten μg of plasmid pOJ108 DNA was digested in 10% ~1 of 1X PstI buffer with 50 units of PstI restriction enzyme for 2 hours at 37° C. This PstI digestion of plasmid pOJ108 results in an ~1.0 kb deletion, thereby removing a BamHI site and inactivating the neomycin resistance-conferring gene. Upon transformation of E. coli SF8 with the plasmid DNA, the resultant transformants were isolated and identified and the plasmid pOJ111 DNA was used to construct cosmid cos111. A restriction site and function map of plasmid pOJ111 is presented in FIG. 10 of the accompanying drawings.

D. Preparation of ScaI-HindIII-Digested Plasmid DNA

About 5 μg of plasmid pOJ111 DNA were mixed with 100 μl 1X reaction buffer (150 mM NaCl, 6 mM TrisHCl pH 7.5, 6 mM $MgCl_2$ and 6 mM Dithiothreitol), and 3 μl (~50 units) of ScaI restriction enzyme and the resulting reaction was incubated at 37° C. for 2 hours. The DNA was extracted with phenol and Sevag, precipitated with ethanol and resuspended in 20 μl of TE. The DNA was resuspended in HindIII buffer and then cut with 50 units of HindIII restriction enzyme at 37° C. for 2 hours. After extraction with phenol and Sevag, the DNA was precipitated with ethanol and resuspended in 20 μl of TE.

Ten μg of plasmid pKC462A DNA were digested with HindIII and ScaI (increased to 70 units) restriction enzymes as taught above. This double digestion generates the desired HindIII-ScaI fragment containing the multiple cos sites and part of the ampicillin resistance-conferring gene. After the reaction ~3 μl (~45 units) of XhoI restriction enzyme were added to the reaction, which was then incubated at 37° C. for 2 hours. This XhoI digestion serves to reduce the likelihood of parental plasmids from reappearing. The digested DNA was isolated as taught above.

E. Ligation of Fragments to Construct Cosmid cos111 and Transformation of *E. coli* K12 SF8

Figure 11:
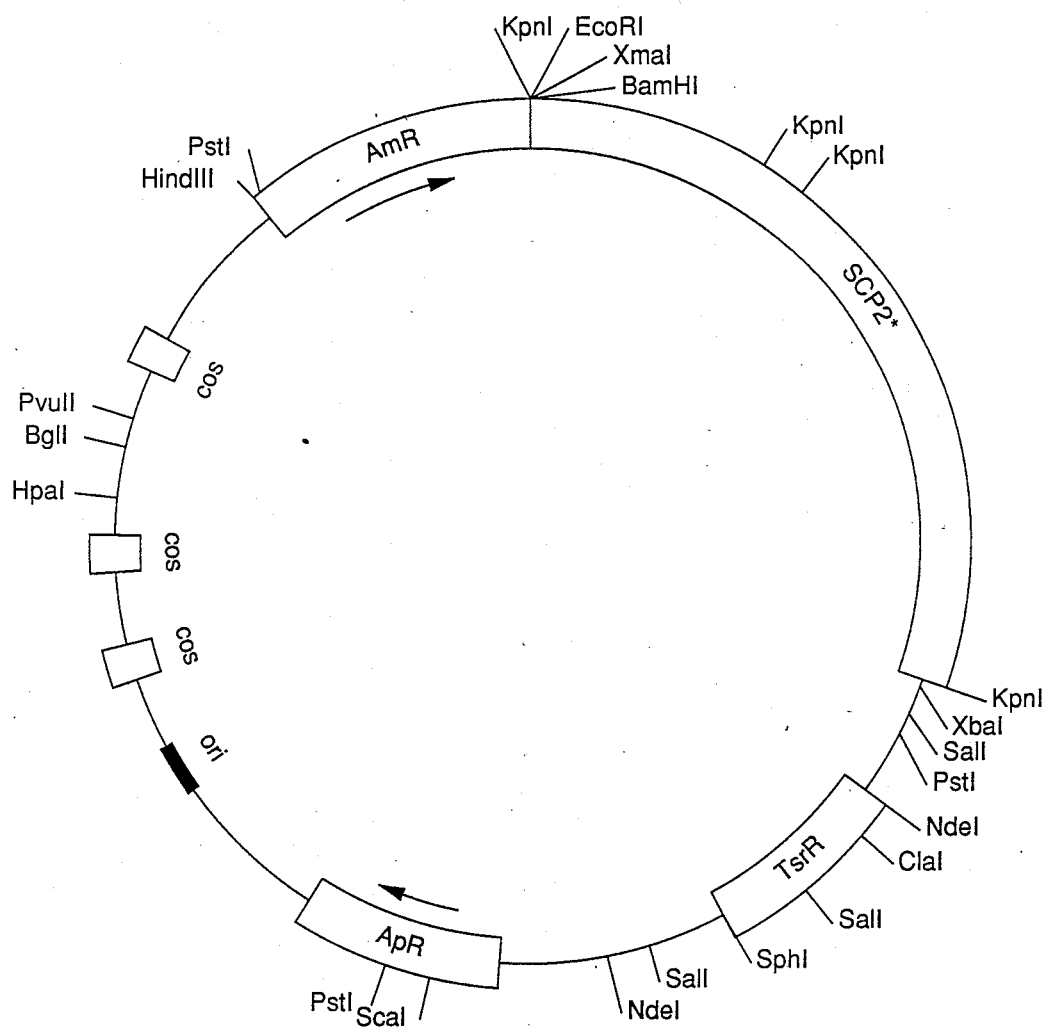
FIG. 11 is a restriction site and function map of cos111.

Five μl of the ScaI-HindIII restriction fragments of plasmid pOJ111 prepared in Example 14D and 5 μl of the ScaI-HindIII digest of cosmid pKC462A prepared in Example 14D were mixed together, and ligated. This ligation mix was used to transform *E. coli* K12 SF8. The desired *E. coli* K12 SF8/cos111 transformants were identified by their apramycin-resistant phenotype and by restriction enzyme analysis of their cosmid DNA. Cosmid DNA was isolated from the transformants in substantial accordance with the prqcedure of Example 1. A restriction site and function map of cos111 is presented in FIG. 11 of the accompanying drawings.

EXAMPLE 15

Construction of *Streptomyces lividans* TK23/cos111

About 1 μg of the DNA from Example 14 and 200 μl of protoplasts of *Streptomyces lividans* TK23 (NRRL 15826) were individually mixed in substantial accordance with the teaching of Example 7. The identity of the desired *S. lividans* TK23/cos111 transformants was conventionally confirmed by initially selecting for the apramycin-resistant phenotype and then replicating those apramycin-resistant colonies to select for thiostrepton resistant colonies.

The transformant colonies were isolated according to known procedures, culture, and then coventionally identified by restriction enzyme and agarose gel electrophoretic analysis of their constitutive cosmids (Maniatis et al., 1982).

EXAMPLE 16

Construction of Plasmid pHJL202

The plasmid pHJL202 contains the streptomycetes replicon from plasmid SCP2* (Bibb et al., 1977, *Molec. Gen. Genet.* 154:155), as well as neomycin resistance and ampicillin resistance genes. The construction of pHJL202 is disclosed below.

A. Partial KpnI Digestion of Plasmid pJL192

About 13 μl (~3.25 μg) of plasmid pJL192 DNA, isolated from *E. coli* K12 C600$R_K$-$M_K$- (NRRL B-15040) and prepared according to the teaching of Example 1, 25 μl water, 5 μl BSA, 5 μl 10X KpnI restriction buffer and 2 μl KpnI enzyme were mixed and incubated at 37° C. for 45 minutes. A 10 μl aliquot was removed, mixed with 40 μl water and heated for 10 minutes to inactivate the enzyme. This protocol produces all possible reaction products ranging from molecules that have not been cleaved by the KpnI restriction enzyme to those that have been completely digested by the KpnI restriction enzyme. The DNA was precipitated with 1/10 volume 3M NaOAc pH 8 and 2 volumes ethanol and then frozen at −70° C. for 1 hour.

B. Ligation

The precipitate was collected, washed twice, air dried and then resuspended in 20 μl water. About 6 μl of the reaction was removed and mixed with a solution of 20 μl 5X kinase/ligase buffer (250 mM TrisHCl pH 7.8, 25% Glycerol, 25 mM Dithiothreitol, and 50 mM $MgCl_2$) 40 μl 0.66M ATP pH 7.4, 33 μl water and 1 μl T4 DNA ligase and incubated at 15° C. for 72 hours to promote self-circularization. After incubation, 50 μl were removed from the reaction and the reaction was terminated by increasing the temperature at 70° C. for 10 minutes. The reaction products were precipitated as above and resuspended in 15 μl water.

C. Transformation

Frozen, competent *E. coli* K12 C600$R_K$-$M_K$- cells were thawed in an ice bath and mixed in a ratio of 0.1 ml of cells to 0.05 ml of plasmid DNA and 37.5 μl of 0.1X SSC (0.015M NaCl, 0.0015M Sodium Citrate at pH 7). The transformation mixture was chilled on ice for 20 minutes, heat shocked at 42° C. for 1 minute and chilled on ice for 10 minutes. The samples were then diluted with 0.85 ml of L-broth, incubated at 37° C. for 1.5 hours, spread on L-agar containing ampicillin (50 μg/ml) and incubated for 18 hours at 37° C. The resulting colonies of correct phenotype, ampicillin resistant ($Ap^R$) and tetracycline sensitive ($Tc^S$), were screened for plasmid size in substantial accordance with the method of in-the-well-lysis as described by Eckhardt et al., 1978, *Plasmid* 1:584. The ampicillin resistant and tetracycline sensitive colonies containing the desired ~18 kb plasmid were isolated according to known procedures, cultured, and used to purify covalently closed circular DNA which was then conventionally identified by restriction enzyme and AGE analysis of the constitutive plasmids. The identified *E. coli* K12 C600$R_K$-$M_K$-/pHJL202 transformants were then used for subsequent production and isolation of plasmid pHJL202 according to the teaching of Example 1 except that strains containing the desired pHJL202 plasmid were used instead of *E. coli* K12 DH1/pKC420.

EXAMPLE 17

Construction of Cosmid pKC473

To obtain the cosmid backbone used in the construction of cosmid pKC473, pKC420 DNA can be conventionally treated with EcoRI and BamHI restriction enzymes in accordance with the conditions recommended by the enzyme manufacturer. The resulting fragments can then be ligated to a gel-purified ~375 bp EcoRI-BamHI restriction fragment from plasmid pBR322 which contains a portion of the tetracycline resistance gene. The ligation products are used to transform *E. coli* in substantial accordance with the teaching of Example 2C and transformants having tetracycline resistant ($Tc^R$) ampicillin sensitive ($Ap^S$) phenotypes are selected. These transformants can then be conventionally cultured for subsequent production and isolation of their cosmid DNA.

Next, the ~752 bp EcoRI-PstI fragment containing a portion of the ampicillin resistance gene from the above-constructed cosmid was deleted. The apramycin resistance gene from plasmid pKC222 (Rao et al., 1983, *Antimicrobial Agents and Chemotherapy* 24(5):689–695) was subcloned into the deleted EcoRIPstI region of the cosmid on an ~1500 bp EcoRI-PstI fragment. The ligated material was used to transform *E. coli* K12 DH1. The identity of the desired transformants was conventionally confirmed by initially selecting for $Tc^R$ phenotype and then replicating those $Tc^R$ colonies to select for Am$^R$ colonies. The resultant *E. coli* K12 DH1/pKC473 transformants were conventionally cultured for subsequent production and isolation of cosmid pKC473.

EXAMPLE 18

Construction of Cosmid Shuttle Vector pKC505

Cosmid pKC505 was constructed from fragments of cosmid pKC473 and plasmid pHJL202. The construction of cosmid pKC505 is illustrated by flow chart in FIG. 12 of the accompanying drawings.

The two vectors, pKC473 and pHJL202, were individually treated with BamHI and EcoRI restriction enzymes to generate linear fragments. These digests were mixed and the fragments ligated and used to transform *Streptomyces ambofaciens* selecting for Am$^R$ colonies. The resulting plasmid was designated pKC505. In this vector, the ~12.8 kb fragment coding the SCP2* replication and fertility functions replaced the ~375 bp fragment coding for the TcR gene of plasmid pKC473.

Cosmid pKC505 was subsequently shuttled into *E. coli* DH1 to verify the structure of the cosmid by restriction enzyme analysis. Cosmid pKC505 was back-transformed into *S. ambofaciens* to check its ability to function as a shuttle vector.

EXAMPLE 19

Construction of Cosmid pKC513

Cosmid pKC513 is a cosmid shuttle vector which comprises the *E. coli* R6K replicon and lambda cos sites from pcos2EMBL (Poustka et al. 1984), the Streptomyces replicon and apramycin resistance gene from pKC498 (a deletion derivative of cosmid pKC462A), and the Tn5 neomycin resistance gene.

The intermediate vector pKC498 was constructed by digesting pKC462A DNA with HindIII restriction enzyme to remove the neomycin resistance conferring gene. The reaction mixture was ligated at low DNA concentration (1 μg/ml) to promote self-circularization. *E. coli* DH1 was transformed with the ligation mix with selection for ampicillin resistant colonies. These Ap$^R$ colonies were then screened for neomycin sensitivity. One of these resulting colonies was cultured and used to isolate plasmid DNA; the isolated plasmid was designated pKC498.

Figure 13:
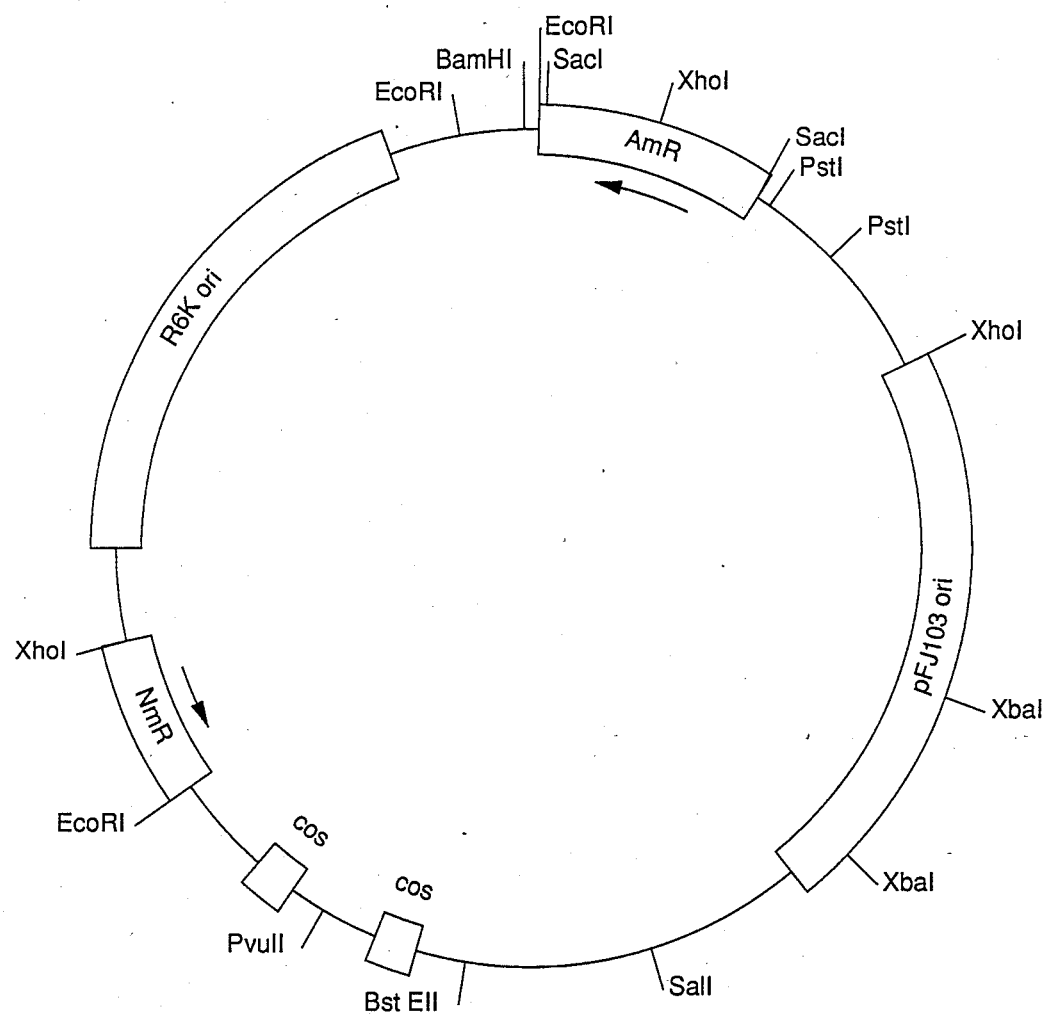
FIG. 13 is a restriction site and function map of cosmid pKC513.

Next, cosmids pKC498 and pcos2EMBL were individually treated with BamHI and SalI restriction enzymes to generate BamHI-SalI fragments. The reaction mixtures were ligated and used to transform *E. coli* DH1. The identity of the desired transformants was conventionally confirmed by initially selecting for Am$^R$ phenotype and then screening those Am$^R$ colonies for neomycin resistance. From one of the Am$^R$ Nm$^R$ colonies, a cosmid was isolated and designated pKC513. In this cosmid, the small BamHI-SalI (~277 bp) fragment of pcos2EMBL containing part of the Tc$^R$ gene is replaced by the ~5.4 kb BamHI-SalI fragment from pKC498 that includes the Am$^R$ gene and the pFJ103 Streptomyces replicon. A restriction site and function map of the cosmid is presented in FIG. 13 accompanying drawings.

EXAMPLE 20

Construction of Cosmids pKC531 and pKC532

Figure 12:
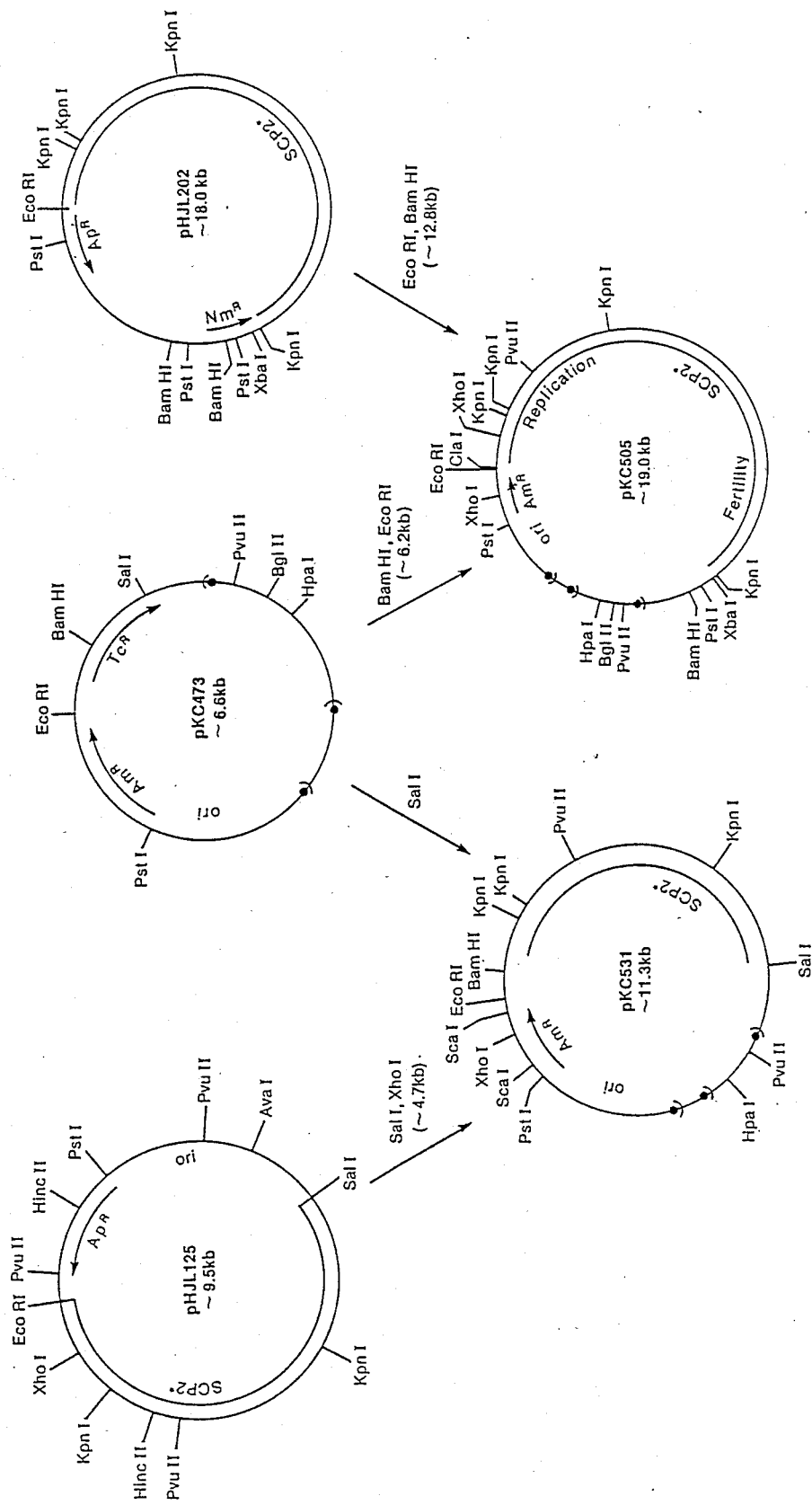
FIG. 12 is an illustrative flow chart of the construction of cosmids pKC505 and pKC531.

FIG. 12 illustrates the construction of the cosmid shuttle vector pKC531. The SCP2* replicon was isolated on an ~4.7 kb XhoI-SalI fragment from plasmid pHJL125 which is described by Hershberger et al., December 1983, "Uses of Recombinant DNA", *Ann. N.Y. Acad. Sci.* p. 31–46. This replicon-containing fragment was inserted into SalI-digested pKC473 and the resulting constructions were used to transform *Streptomyces griseofuscus*. The identity of the desired transformants was confirmed by selecting for Am$^R$ phenotype and individual cosmids were identified by restriction enzyme analysis. A restriction site and function map of cosmid pKC531 is depicted in FIG. 12 of the accompanying drawing. Cosmid pKC532 differs only in the orientation of the SCP2* replicon-containing fragment.

EXAMPLE 21

Conjugation in Streptomyces

Cosmid pKC505 was transformed into *Streptomyces lividans* TK24 in substantial accordance with the teaching of Example 7 to produce an apramycin resistant, spectinomycin sensitive and streptomycin resistant donor strain. Any Streptomyces strain can be utilized as a recipient in this example provided that it is apramycin sensitive and carries a selectable resistance determinant that is not present in the donor. In this example, an *S. lividans* strain, 3104, was used that is apramycin sensitive and spectinomycin resistant (Spc$^R$) In addition, the use of a particular donor strain is not critical to practice the present invention so long as it can be selected under conditions permitting the growth of the recipient strain.

Both Streptomyces cultures TK24 (pKC505) and 3104 were separately grown in TSB at 34° C. After homogenizing and sonicating to disrupt the aggregates, the cultures were mixed in a 1:1 ratio and spread on R2 plates. These plates were incubated at 30° C. until sporulation occurred at around day seven. The spores were harvested and analyzed for donor (Am$^R$), recipient (Spc$^R$), and recombinants (Am$^R$, Spc$^R$) on appropriately supplemented TSA plates. The results given in Table 1 indicate that only recipient cells will grow on spectinomycin supplemented plates and only donor cells will grow on apramycin supplemented plates and neither will grow on spectinomycin and apramycin supplemented plates. Thus, recombinants are identified as those which grow on spectinomycin and apramycin supplemented plates.

TABLE 1

| | CFU/ml Under Different Selection Conditions | | | |
|---|---|---|---|---|
| Strain | None | Spc | Am | Spc Am |
| TK24 | $1.5 \times 10^8$ | $4.7 \times 10^2$ | $<10^1$ | $<10^1$ |
| TK24 (pKC505) | $6.3 \times 10^7$ | $2.4 \times 10^2$ | $1.7 \times 10^7$ | $4.5 \times 10^1$ |
| 3104 | $8.0 \times 10^7$ | $9.1 \times 10^7$ | $<10^1$ | $<10^1$ |
| TK24 (pKC505) + 3104 | $1.5 \times 10^8$ | $4.8 \times 10^7$ | $1.9 \times 10^7$ | $2.3 \times 10^3$ |

Transfer frequency expressed as a ratio of Spc Am/Am was $1.2 \times 10^{-4}$
Transfer frequency expressed as a ratio of Spc Am/Spc was $4.8 \times 10^{-5}$

EXAMPLE 22

Construction of Cosmid Shuttle Vector pKC578

A. PstI Digestion of pUC12

About 5 μg pf pUC12 (Vieira and Messing, 1982, *Gene* 19:259) were digested in 1X PstI buffer (100 mM NaCl, 10 mM Tris-HCl pH 7.5, 10 mM MgCl$_2$ and 1 mM dithiothreitol) in a total volume of 50 μl with 10 units of PstI restriction endonuclease. The mixture was incubated at 37° C. for about 1 hour and then the reaction was terminated by incubation at 70° C. for 10 minutes.

B. PstI Digestion of pKC222

About 5 μg of pKC222 (Rao et al., 1983, *Antimicrob. Agents Chemother.* 24:689) were digested with 10 units of PstI in substantial accordance with the teaching of the above example.

C. Ligation and Construction of *E. coli* JM109/pKC404

About 1 μg each of PstI-digested pUC12 and pKC222 DNA were ligated in a 20 μl reaction in substantial accordance with the teaching of Example 2C. The ligated DNA was used to transform DH1 in substantial accordance with the transformation protocol of Example 2C. The transformants were selected for $Ap^R Am^R$ and the desired transformants were screened for lac operator and identified by the PstI digestion of the plasmid DNA. The resultant *E. coli* K12 DH1/pKC404 transformants were conventionally cultured for subsequent production and isolation of pKC404.

D. SalI Digestion of pKC404

About 5 μg of pKC404 were digested in 1X SalI buffer (150 mM NaCl, 6 mM Tris-HCl pH 7.9, 6 mM $MgCl_2$, 6 mM dithiothreitol) in a total volume of 50 μl with 10 units of SalI restriction endonuclease (New England Biolabs). The mixture was incubated at 37° C. for about 1 hour and then the reaction was terminated by extraction with phenol and Sevag, and the DNA was precipitated with ethanol. The precipitate was collected by centrifugation, dried and then resuspended in 5 μl of 5 mM NaCl.

About 1 μg of the SalI cut pKC404 was treated with 1 unit of Mung Bean Nuclease (New England Biolabs) in a total volume of 100 μl (30 mM Sodium acetate pH 4.6, 50 mM Sodium chloride, 1 mM zinc chloride). The mixture was incubated at 37° C. for 10 minutes. The reaction was terminated by extracting the DNA with phenol and Sevag. The DNA was precipitated with ethanol and dissolved in 5μl of 5 mM NaCl.

E. EcoRI and NruI Digestion of pcos2EMBL

About 5 μg of pcos2EMBL were digested in a buffer (100 mM NaCl, 10 mM Tris-HCl pH 7.5, 10 mM $MgCl_2$ and 10 mM dithiothretiol) in a total volume of 50 μl with 10 units each of EcoRI and NruI restriction endonuclease. The mixture was incubated at 37° for about 1 hour and then the reaction was terminated as described in Example 22D. About 1 μg of the EcoRI-and NruI-cut DNA was treated with Mung Bean Nuclease and dissolved in 5 μl of 5 mM NaCl as described in Example 22D.

F. Ligation and Construction of *E. coli* K12 SF8/pKC572

About 1 μg of EcoRI- and-NruI digested and Mung Bean Nuclease treated pcos2EMBL were ligated with 1 μg of SalI-digested and Mung Bean Nuclease treated pKC404 in substantial accordance with the teaching of Example 2C. The ligated DNA was used to transform *E. coli* SF8; the transformants were initially selected for $Am^R$ and subsequently selected for in vivo packaging by bacteriophage λ. The desired transformants were identified by HindIII, XhoI, AhaIII, BamHI and PvuII restriction enzyme digests. The resultant *E. coli* K12 SF8/pKC572 was conventionally cultured for subsequent production and isolation of pKC572.

G. HindIII and BamHI Digestion of pRLM5 and Isolation of the ~4.0 kb Fragment Containing $imm^{434}$ Replication Functions About 10 μg of pRLM5 (Wold et al., 1982, *Proc. Natl. Acad. Sci. USA* 79:6176) were digested in 100 mM NaCl, 10 mM Tris-HCl pH 7.5, 10 mM $MgCl_2$ and 10 mM dithiothreitol in a total volume of 100 μl with 20 units each of HindIII and BamHI restriction endonuclease. The mixture was incubated at 37° C. for about 1 hour and the digestion was terminated by incubating at 70° C. for 10 minutes. The DNA fragments were separated on a 1% low-melting agarose gel. The ~4.0 kb fragment was isolated by melting the agarose segment containing the fragment at 70° C. for 5 minutes, followed with two phenol and two Sevag extractions, and then precipitating the DNA with ethanol. The precipitate was collected by centrifugation, dried in vacuo and then dissolved in 5 μl of 5 mM NaCl.

H. HindIII and BamHI digestion of pKC572 and Isolation of the ~3.0 kb fragment containing the $Am^R$ gene and λ cos sites About 10 μg of pKC572 were digested with HindIII and BamHI restriction endonucleases, as described in the above section. The ~3.0 kb fragment that includes the $Am^R$ gene and double cos sites was isolated as described in the above section and then dissolved in 5 μl of 5 mM NaCl.

I. Ligation and Construction of *E. coli* K12 BE827/pKC580

About 1 μg each of the ~4 kb fragment as described in Section G and the ~3 kb fragment described in Section H can be ligated in substantial accordance with the teaching of Example 2C. The ligated DNA is then used to transform *E. coli* K12 BE827 (ATCC 31911) selecting for $Am^R$ transformants. The structure of the plasmid in these transformants can be verified by HindIII and BamHI digestion and by in vivo packaging by designated pKC580.

J. BamHI Digestion of pKC580

About 5 μg of pKC580 DNA can be digested with 10 units of BamHI as described in Section 2G. The digestion is then terminated by incubating at 70° C. for 10 minutes.

K. BclI Digestion of Plasmid pSAM2

Plasmid pSAM2 is described by Pernodet et al., 1984, *Mol. Gen. Genet.* 198:35 and the *S. ambofaciens* strain containing the plasmid is available from the John Innes Institute, Norwich, United Kingdom. About 5 μg of the plasmid DNA was digested with BclI restriction enzyme in substantial accordance with the teaching of Example 2B. After the reaction was terminated, the DNA was extracted, precipitated and dissolved in 5 μl of 5 mM NaCl.

L. Ligation and Construction of *Streptomyces griseofuscus*/pKC578

Figure 14:
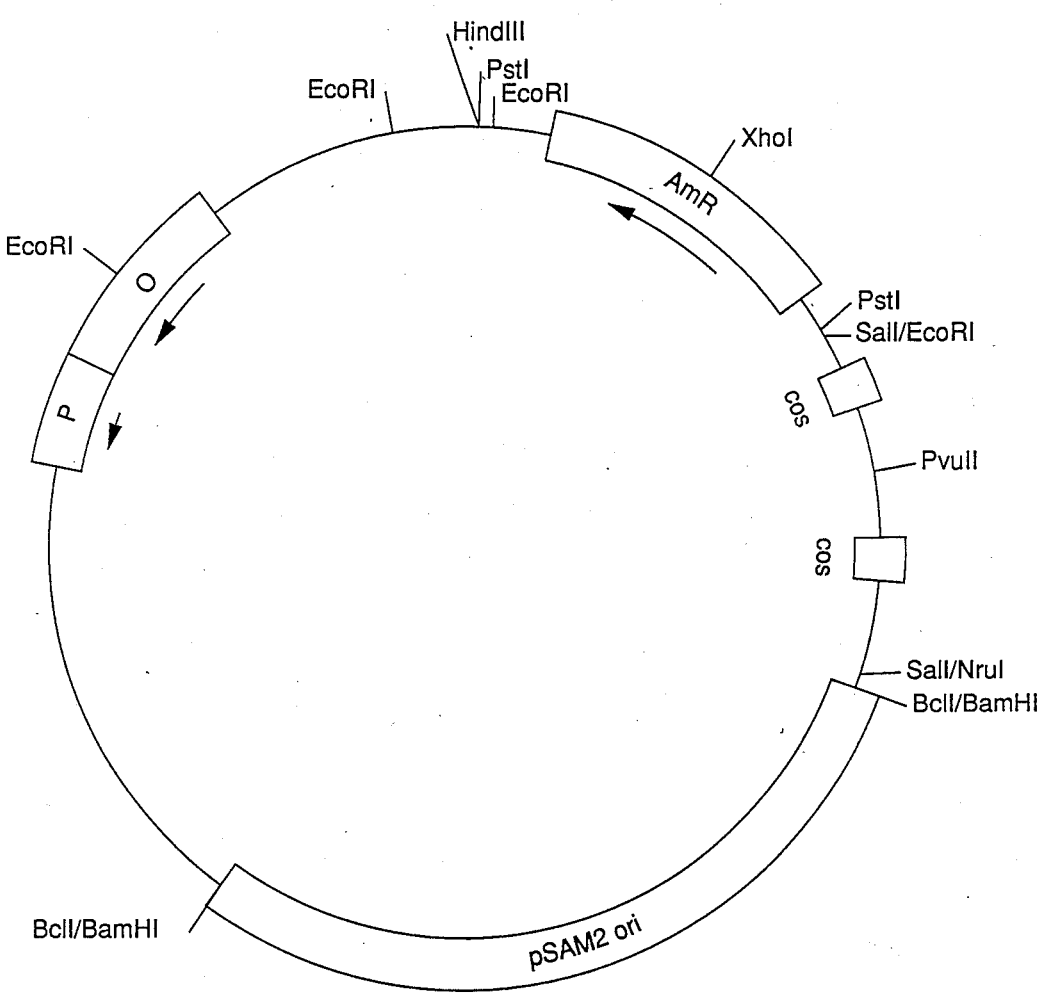
FIG. 14 is a restriction site and function map of cosmid pKC578.

Mix about 1 μg each of BamHI digested pKC580 and BclI-digested pSAM2 in 20 μl ligation mixture and ligate them in substantial accordance with the teaching of Example 2C. The ligation is terminated by incubating at 70° C. for 10 minutes. The ligated material can then be used to transform *Streptomyces griseofuscus* C581 protoplasts selecting for Am$^R$ transformants. The transformants are picked and grown in TSB supplemented with apramycin and used to make plasmid DNA. This plasmid DNA is then shuttled into *E. coli* DH1 and the plasmid structure is verified by restriction enzyme analysis and its function analyzed by cosmid cloning and shuttling into *S. griseofuscus*. A restriction site and function map of pKC578 is presented in FIG. 14 of the accompanying drawings.

We claim:

1. A recombinant double standard DNA cosmid shuttle vector comprising:
   (a) a replicon that is functional in *E. coli*,
   (b) a replicon that is functional in Streptomyces,
   (c) a double stranded DNA segment that contains two or more cos sequences of bacteriophage lambda, and
   (d) one or more DNA segments that convey resistance to at least one antibiotic when transformed into a sensitive restrictionless host cell.

2. The recombinant DNA cosmid shuttle vector of claim 1 selected from the group consisting of pKC420, pKC427, pKC428, pKC448, pKC462, and pKC467.

3. The recombinant DNA cosmid shuttle vector of claim 2 which is pKC420.

4. The recombinant DNA cosmid shuttle vector of claim 2 which is pKC427.

5. The recombinant DNA cosmid shuttle vector of claim 2 which is pKC428.

6. The recombinant DNA cosmid shuttle vector of claim 2 which is pKC448.

7. The recombinant DNA cosmid shuttle vector of claim 2 which is pKC462.

8. The recombinant DNA cosmid shuttle vector of claim 2 which is pKC467.

9. The recombinant DNA cosmid shuttle vector of claim 1 wherein the *E. coli* replicon is selected from the group consisting of replicon-containing fragments of plasmids pBR322, pBR324, pBR325 and pBR328.

10. The recombinant DNA cosmid shuttle vector of claim 1 wherein the Streptomyces replicon is selected from the group consisting of replicon-containing fragments of plasmids SCP2, SCP2*, SLP1, pEL103 and pFJ265.

11. A transformed host cell selected from the group consisting of restrictionless Streptomyces and *E. coli*, said host cell comprising a recombinant DNA cosmid shuttle vector of claim 1.

12. A transformed host cell selected from the group consisting of restrictionless Streptomyces and *E. coli*, said host cell comprising a recombinant DNA cosmid shuttle vector of claim 2.

13. The transformed host cell of claim 12 which is restrictionless Streptomyces.

14. The transformed host cell of claim 13 which is selected from the group consisting of *Streptomyces ambofaciens, Streptomyces aureofaciens, Streptomyces cinnamonesis, Streptomyces fradiae, Streptomyces granuloruber, Streptomyces lividans,* and *Streptomyces griseofuscus.*

15. The transformed host cell of claim 13 which is *Streptomyces ambofaciens*/pKC420.

16. The transformed host cell of claim 13 which is *Streptomyces ambofaciens*/pKC448.

17. The transformed host cell of claim 13 which is *Streptomyces ambofaciens*/pKC462.

18. The transformed host cell of claim 13 which is *Streptomyces fradiae*/pKC420.

19. The transformed host cell of claim 13 which is *Streptomyces fradiae*/pKC448.

20. The transformed host cell of claim 13 which is *Streptomyces lividans*/pKC420.

21. The transformed host cell of claim 13 which is *Streptomyces lividans*/pKC448.

22. The transformed host cell of claim 13 which is *Streptomyces lividans*/pKC462.

23. The transformed host cell of claim 13 which is *Streptomyces lividans*/pKC467.

24. The transformed host cell of claim 12 which is *E. coli*.

25. The transformed host cell of claim 24 which is *E. coli* K12 SF8/pKC420.

26. The transformed host cell of claim 24 which is *E. coli* K12 SF8/pKC448.

27. The transforled host cell of claim 24 which is *E. coli* DH1/pKC462.

28. A method for using the cosmid shuttle vector of claim 1 to construct genomic DNA libraries, said method comprising:
    (a) ligating a genomic DNA segment into said cosmid shuttle vector,
    (b) packaging said ligated cosmid into bacteriophage lambda particles,
    (c) transducing said packaged cosmid into E. coli, and
    (d) transforming the recombinant cosmid into a Streptomyces host cell.

29. A method according to claim 28, wherein said cosmic shuttle vector DNA is selected from the group consisting of pKC420 pKC427, pKC428, pKC448, pKC462 and pKC467.

30. The method of claim 29, wherein said cosmid shuttle vector is p-KC420.

31. The method of claim 29, wherein said cosmid shuttle vector is p-KC448.

32. The method of claim 29 wherein said cosmid shuttle vector is pKC-462.

33. The method of claim 29 wherein said cosmid shuttle vector is pKC467.

34. The recombinant DNA cosmid shuttle vector of claim 1 which is pKC462A.

35. The recombinant DNA cosmid shuttle vector of claim 1 which is pKC467A.

36. The recombinant DNA cosmid shuttle vector of claim 1 which is cos111.

37. The transformed host cell of claim 11 which is *Streptomyces ambofaciens*/pKC462A.

38. The transformed host cell of claim 11 which is *Streptomyces lividans*/cos111.

39. The transformed host cell of claim 11 which is *E. coli* K12 SF8/pKC462A.

40. The transformed host cell of claim 11 which is *E. coli* K12 SF8/pKC467A.

41. The transformed host cell of claim 11 which is *E. coli* K12 SF8/cos111.

42. The method of claim 28 wherein said cosmid shuttle vector is selected from the group consisting of pKC462A and cos111.

43. The recombinant DNA cosmid shuttle vector of claim 1 which is selected from the group consisting of pKC513, pKC531, pKC532, and pKC578.

44. The recombinant DNA cosmid shuttle vector of claim 43 which is pKC513.

45. The recombinant DNA cosmid shuttle vector of claim 43 which is pKC531.

46. The recombinant DNA cosmid shuttle vector of claim 43 which is pKC532.

47. The recombinant DNA cosmid shuttle vector of claim 43 which is pKC578.

48. The transformed host of claim 11 that is *Streptomyces griseofuscus*.

49. The transformed host of claim 48 that is *Streptomyces griseofuscus*/pKC531.

50. The transformed host of claim 48 that is *Streptomyces griseofuscus*/pKC532.

51. The transformed host of claim 48 that is *Streptomyces griseofuscus*/pKC578.

52. The recombinant DNA cosmid shuttle vector of claim 1 which further comprises a DNA segment that contains a Strepomyces fertility factor.

53. The recombinant DNA cosmid shuttle vector of claim 52 wherein the fertility factor is from plasmid SCP2*.

54. The recombinant DNA cosmid shuttle vector of claim 53 which is pKC505.

55. A transformed host cell selected from the group consisting of restrictionless Streptomcyes and *E. coli*. said host cell comprising the recombinant DNA cosmid shuttle vector of claim 54.

56. The transformed host cell of claim 55 which is *Streptomyces griseofuscus*/pKC505.

57. The transformed host cell of claim 55 which is *E. coli* K12 DH1/pKC505.

58. The method of claim 28 wherein said cosmid shuttle vector is selected from the group consisting of pKC505, pKC531, and pKC578.

* * * * *

UNITED STATES PATENT AND TRADEMARK OFFICE
CERTIFICATE OF CORRECTION

PATENT NO. : 4,921,801

DATED : May 1, 1990

INVENTOR(S) : R. Nagaraja Rao
Richard K. Stanzak

It is certified that error appears in the above-identified patent and that said Letters Patent is hereby corrected as shown below:

Column 25, line 12, "standard" should read --stranded--.

Column 26, line 19, "transforled" should read --transformed--.

Column 26, line 32, "cosmic" should read --cosmid--.

Column 26, line 36, "p-KC420" should read --pKC420--.

Column 26, line 38, "p-KC448" should read --pKC448--.

Column 26, line 40, "pKC-462" should read --pKC462--.

Signed and Sealed this

Third Day of March, 1992

Attest:

HARRY F. MANBECK, JR.

*Attesting Officer*     Commissioner of Patents and Trademarks